US006528309B2

(12) United States Patent
Levine

(10) Patent No.: US 6,528,309 B2
(45) Date of Patent: Mar. 4, 2003

(54) VACUUM-MEDIATED DESICCATION PROTECTION OF CELLS

(75) Inventor: Fred Levine, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/812,042

(22) Filed: Mar. 19, 2001

(65) Prior Publication Data

US 2003/0017444 A1 Jan. 23, 2003

(51) Int. Cl.$^7$ .............................. C12N 5/06; C12N 5/08
(52) U.S. Cl. ........................ 435/374; 435/404; 435/366
(58) Field of Search ............................... 435/374, 404, 435/366

(56) References Cited

U.S. PATENT DOCUMENTS

| | | | | |
|---|---|---|---|---|
| 4,683,195 A | | 7/1987 | Mullis et al. .................... 435/6 |
| 4,683,202 A | | 7/1987 | Mullis .......................... 435/91 |
| 4,874,690 A | * | 10/1989 | Goodrich, Jr. et al. .......... 435/2 |
| 4,965,188 A | | 10/1990 | Mullis et al. .................... 435/6 |
| 5,030,560 A | * | 7/1991 | Sinor et al. ................. 435/7.21 |
| 5,641,637 A | * | 6/1997 | Hudak et al. ............... 435/7.24 |
| 6,008,052 A | * | 12/1999 | Davis et al. ................... 436/10 |

OTHER PUBLICATIONS

Guo et al., Trehalose expression cinfers desiccation tolerance on human cells, 1999, Nature America Inc, pp. 168–171.*
Malik et al., Successful preservation of campylobacteraceae and related bacteria by liquid–drying under anaerobic conditions, 1996, Journal of Microbiological Methods, vol. 25, pp. 37–42.*
Allison et al., "Hydrogen bonding between sugar and protein is responsible for inhibition of dehydration–induced protein unfolding," Arch. Biochem. Biophys., 365:289–298 [1999].
Arakawa et al., "The basis for toxicity of certain cryoprotectants: a hypothesis," Cryobiol., 27:401–415 [1990].
Beattie et al., "Trehalose: a cryoprotectant that enhances recovery and preserves function of human pancreatic islets after long–term storage," Diabetes, 46:519–523 [1997].
Berkner, "Expression of heterologous sequences in adenoviral vectors," Curr. Top. Microbiol., 66:1680–1684 [2000].
Billi et al., "Engineering desiccation tolorance in Escherichia coli," Appl. Environ. Microbiol., 6:1680–1684 [2000].
Calabrese et al., "Oxidative stress and antioxidants at skin biosurface: a novel antioxidant from lemon oil capable of inhibiting oxidative damage to the skin," Drugs Exp. Clin. Res., 25:281–287 [1999].
Colaco et al., "Extraordinary stability of enzymes dried in trehalose: simplified molecular biology," Biotechnol., 10:1007–1011 [1992].

Crowe and Crowe, "Stabilization of Membranes in Anhydrobiotic Organisms," in Leopold (ed.), Metabolism and Dry Organisms, (Cornstock Publishing Associates, Ithacs and New York) pp. 188–209 [1986].
Crowe et al., "Interaction of sugars with membranes," Biochim. Biophys. Acta 947:367–384 [1988].
Crowe et al., "Anhydrobiosis," Ann. Rev. Physiol., 54:579–599 [1992].
Crowe et al., "The role of vitrification in anhydrobiosis," Ann. Rev. Physiol., 60:73–103 [1998].
Daw et al., "Membrane leakage of solutes after thermal shock or freezing," Cryobiol., 10:126–133 [1973].
de–Araujo, "The role of trehalose in cell stress," Braz. J. Med. Biol. Res., 29:873–875 [1996].
de Castro and Tunnacliffe, "Intracellular trehalose improves osmotolerance but not desiccation tolerance in mammalian cells," FEBS Lett., 487:199–202 [2000].
Erickson et al., "Mechanisms for the production of DNA damage in cultured human and hamster cells irradiated with light from fluorescent lamps, sunlamps, and the sun," Biochim. Biophys. Acta 610:105–115 [1980].
Freshney, Culture of Animal Cells: A Manual of Basic Technique, (Alan R. Liss, Inc., New York) [1983] not supplied.
Gannt et al., "Fluorescent light–induced DNA crosslinkage and chromatid breaks in mouse cells in culture," Proc. Natl. Acad. Sci. USA, 75:3809–3812 [1978].
Guo et al., "Trehalose expression confers desiccation tolerance on human cells," Nat. Biotechnol., 18:168–171 [2000].
Hallsworth and Magan, "Effects of KCI concentration on accumulation of acyclic sugar alcohols and trehalose in conidia of three entomopathogenic fungi," Lett. Appl. Microbiol., 18:8–11 [1994].
Hallsworth and Magan, "Manipulation of intracellular glycerol and erythritol enhances germination of conidia at low water availability," Microbiol., 141:1109–1115 [1995].
Hirata et al., "Effects of trehalose in canine lung preservation," Surgery, 115:102–107 [1994].
Kaasen et al., "Analysis of the otsBA operon for osmoregulatory trahalose synthesis in Escherichia coli and homology of the OtsA and OtsB proteins to the yeast trehalose–6–phosphate synthase/phosphatase complex," Gene, 145:9–15 [1994].

(List continued on next page.)

Primary Examiner—James Ketter
Assistant Examiner—D Sullivan
(74) Attorney, Agent, or Firm—Medlen & Carroll LLP

(57) ABSTRACT

The present invention provides methods and compositions for the protection and storage of cells. In particular, the present invention provides methods and compositions for the vacuum-mediated desiccation protection of mammalian cells. In particularly preferred embodiments, cells are treated with a carbohydrate (e.g., a disaccharide) prior to vacuum-mediated desiccation.

26 Claims, 8 Drawing Sheets

OTHER PUBLICATIONS

Leibowitz et al., "Gene transfer to human pancreatic emdocrine cells using viral vectors," *Diabetes*, 48:745–753 [1999].

Leslie et al., "Trehalose lowers membrane phase transitions in dry yeast cells," *Biochim. Biophys. Acta*, 1192:7–13 [1994].

Leslie et al., "Trehalose and sucrose protect both membranes and proteins in intact bacteria during drying," *Appl. Environ. Microbiol.*, 61:3592–3597 [1995].

Lipinski et al., "Repair of oxidative DNA base lesions induced by fluorescent light is defective in xeroderma pigmentosum group A cells," *Nucleic Acids Res.*, 27:3153–3158 [1999].

Moore et al., "Introduction of soluble protein into the class I pathway of antigen processing and presentation," *Cell*, 54:777–785 [1988].

Murakami et al., "Molecular genetic mechanisms of the life span manipulation in *Caenorhabditis elegans*," *Ann. N. Y. Acad. Sci.*, 908:40–49 [2000].

Okada and Rechsteiner, "Introduction of macromolecules into cultured mammalian cells by osmotic lysis of pinocytic vesicles," *Cell*, 29:33–41 [1982].

Ozawa, "Mitochondrial genome mutation in cell eath and aging," *J. Bioenerg. Biomember.*, 31:377–390 [1999].

Pansarasa et al., "Age–dependent changes of antioxidant activities and markers of free radical damage in human skeletal muscle," *Free Radic. Biol. Med.*, 27:617–622 [1999].

Pellerin–Mendes et al., "*In vitro* study of the protective effect of trehalose and dextran during freezing of human red blood cells in liquid nitrogen," *Cryobiol.*, 35:173–186 [1997].

Pelletier and Sonenberg, "Internal initiation of translation of eukaryotic mRNA directed by a sequence derived from poliovirus RNA," *Nature*, 334:320–225 [1988].

Renard et al., "Improvement of motility and fertilization potential of postthaw human sperm using glutamine," *Cryobiol.*, 33:311–319 [1996].

Rudge, "Maintenance of Bacteria by Freeze–Drying," in Maintenance of Microorganisms, 2nd ed., Kirsop and Doyle (eds.), Academic Press, London, pp. 31–44 [1991].

Singer and Lindquist, "Thermotolerance in *Saccharomyces cerevisiae*: the yin and yang of trehalose," *Mol. Cell.*, 1:639–648 [1998].

Solomon et al., "Desiccation tolerance of *Muellerius cf. capillaris* (nematoda: protostrongylidae) first–stage larvae," *J. Parasitol.*, 84:802–805 [1998].

Spessot et al., "Cloning of the herpes simplex virus ICP4 gene in an adenovirus vector: effects on adenovirus gene expression and replication," *Virol.*, 168:378–387 [1987].

Storey et al., "Comparison of glycerol, other polyols, trehalose, and raffinose to provide a defined cryoprotectant medium for mouse sperm cryopreservation," *Cryobiol.*, 37:46–58 [1998].

Uritani et al., "Protective effect of disaccharides on restriction endonucleases during drying under vacuum," *J. Biochem. (Tokyo)*, 117:774–779 [1995].

Wang et al., "Development of a VSV–G protein pseudotyped retroviral vector system expressing dominant oncogenes from a lacO–modified inducible LTR promoter," *Gene*, 182:145–150 [1996].

Weimken, "Trahalose in yeast, stress protectant rather than reserve carbohydrate," *Antonie Van Leeuwenhoek*, 58:209–217 [1990].

Puhlev et al., "Desiccation tolerance in human cells," *Cryobiol.*, 42:207–217 [2001].

* cited by examiner

A.

B.

SEQUENCE LISTING

<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
ccgctcgagc accaccatga cagaaccgtt aaccgaaacc      40

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
cggaattctt agatactacg actaaacgac      30

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
tgctctagac caccatgagt cgtttagtcg tagtatctaa c      41

```
<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
agcggccgcc tacgcaagct ttggaaaggt agc                              33
```

VACUUM-MEDIATED DESICCATION PROTECTION OF CELLS

FIELD OF THE INVENTION

The present invention provides methods and compositions for the protection and storage of cells. In particular, the present invention provides methods and compositions for the vacuum-mediated desiccation protection of cells.

BACKGROUND OF THE INVENTION

Initially devised as a method of studying the behavior of animal cells in a system that is free of systemic variations, tissue culture has been in use since the early 1900s (See e.g., Freshney, I., *Culture of Animal Cells: A Manual of Basic Technique*, Alan R. Liss, Inc., New York [1983], at page 1). Although the first work focused on tissues maintained in vitro, cultures of cells have become more commonly used over time. The development of tissue culture has contributed significantly to the fields of virology and oncology, although it has also played an essential role in elucidating various intracellular activities (e.g., DNA transcription, protein synthesis, etc.), intracellular flux (e.g., RNA movement, translocation of hormone receptor complexes, fluctuations in metabolite pools, etc.), cellular and organismal ecology (e.g., infection, drug interactions, and population kinetics, membrane flux, etc.), and cell-cell interactions (embryonic induction, cell population kinetics, cell-cell adhesion, etc.).

Cell cultures provide means to work with cells in controlled environments. For example, the pH, temperature, osmotic pressure, $O_2$ tension, $CO_2$ tension and other variables are controllable within the cell culture environment. With advances in media formulations, the culture media used to grow cell cultures may also be defined and controlled. Among their many advantages over the use of experimental animals, cell cultures facilitate the direct observation of effects of compounds/reagents on cells, typically at a lower and defined concentration. Thus, cell cultures are more economical than animal studies, in which losses of the test compound under investigation often occur due to excretion and/or distribution to other tissues.

However, there are disadvantages associated with cell cultures. The procedures must be carried out under aseptic conditions to prevent contamination by bacteria and fungi. In addition, unlike bacteria, cells from multicellular animals do not normally exist in isolation and require a complex environment in order to sustain their existence in vitro. Furthermore, cell cultures maintained in in vitro tend to be unstable. Short-term cultures tend to be heterogenous with regard to growth rate and other characteristics, even if the cells are genetically stable. This can lead to variability between passages of the culture. Indeed, selection and phenotypic drift occur in cultures, although by about the third passage, the cell culture tends to be become more stable. However, if transformed cells are present in the culture, they will overgrow their normal counterparts.

Indeed, during the development of a cell line from a primary culture and during subsequent maintenance of the culture, phenotypic and genotypic instability is typically observed. This instability is the result of culture condition variations, selective overgrowth of some cells in the population, and genetic variation. As it is important to standardize the culture so that the cell population remains as stable as possible over time, seed stocks of the cell culture are often preserved. Cell preservation minimizes the genetic drift in cultures, as well as serving to avoid senescence and guarding against contamination, as well as providing a stock culture, should the "working" culture become contaminated, change, or otherwise unusable.

Freezing is a commonly used method to store cell cultures. In freezing, water is made unavailable to the cells, and the dehydrated cells are maintained at low temperatures. Damage may be caused to the cells during the cooling stage and/or the subsequent thawing. This damage may be caused either by the concentration of electrolytes through removal of water as ice, or by the formation of ice crystals that shear the cells. Damage may be somewhat limited by adjusting the cooling and warming rates, as well as by adding cryoprotectants (e.g., dimethyl sulfoxide [DMSO], etc.) to the cell suspension. Although various temperatures have been used to store frozen cultures (e.g., $-20°$ C., $-30°$ C., $-40°$ C., $-70°$ C., $-140°$ C., and $-196°$ C.), poor results are usually observed at temperatures above $-30°$ C.

Freezing in liquid nitrogen has been widely used for many organisms and cell cultures and is currently recommended for storage of valuable seed stock cultures. There are numerous advantages to this method, as in many cases, no loss of viability occurs during storage (although some cells may die during cooling and warming). In general, there is no genetic change or loss of characters; and the longevity and stability tends to be maintained. Typically, cells are frozen in small aliquots and maintained in liquid nitrogen or at $-70°$ C. The frozen cells are then thawed and revived for use as needed. However, there are potential problems associated with freezing of cells, as cell viability is affected by the freezing medium used, as well as the temperature of storage (e.g., significant deterioration may occur at storage temperatures as low as $-70°$ C.), and the method of thawing and revival. In addition, improperly sealed glass ampules present an explosion risk during thawing. Additional disadvantages of freezing cultures in liquid nitrogen include the need to continually replenish the liquid nitrogen, the high cost of equipment, and the inconvenience of storing and distributing of large numbers of cultures (e.g., storage space may be problematic).

Desiccation has been widely used as a method to preserve microorganisms. A variety of methods are used, although all depend upon the removal of water from the culture and prevention of rehydration. Although drying methods have been more commonly used with molds than bacteria, some bacteria and yeasts have been successfully preserved using these methods. In the most commonly used methods, the cultures are dried in soil, sand, kieselguhr, and/or silica gel, dried onto paper or gelatin strips or discs, or formed into pre-dried plugs.

Freeze-drying involves the removal of water by sublimination from a frozen culture. Organisms are grown on a suitable growth medium, aliquots are suspended in an appropriate freeze-drying liquid in ampules or vials, and placed in the freeze-drying apparatus, where they are frozen, and exposed to a vacuum. The water vapor from the culture is typically trapped in a refrigerated condenser unit or in phosphorous pentoxide. After freeze-drying, the cultures are sealed in their vials, often under vacuum or in an inert gas, and are stored at room temperature, refrigerated, or frozen. Two methods of freeze-drying are commonly used in industry, namely centrifugal and shelf freeze-drying (See, R. H. Rudge, "Maintenance of Bacteria by Freeze-Drying," in Maintenance of Microorganisms, 2d ed., B. E. Kirsop and A. Doyle (eds.), Academic Press, London, [1991], pp. 31–44).

Although freeze drying has been widely used to preserve various organisms, there are problems associated with this method. For example, glass ampules are generally sealed closed with a flame (e.g., a torch), requiring some care in order to avoid injury to the operator, and some ampules are very difficult to open, requiring filing in order to sufficiently weaken the glass so that the ampule can be broken. This presents risks of contamination of the culture through the introduction of contaminants through the filed area of the ampule, as well as risk of injury to the operator, should the ampule unexpectedly break. Thus, there are major safety considerations associated with the use of currently used freeze drying methods. In addition, these methods have not found use with cell cultures.

Indeed, none of the drying methods has found universal acceptance, as their efficacy appears to be culture-specific (i.e., some cells may not be preserved using these methods, as they become non-viable during the process). For cultures that are suited for preservation by drying, long-term viability is often good, contamination is less likely than with subculturing, and capital equipment costs are small. However, drying methods have not found acceptance in preservation of cell cultures. Thus, there remains a need in the art for compositions and methods for the storage and transport of cell cultures that are easy to use and handle, reliable and cost-effective.

SUMMARY OF THE INVENTION

The present invention provides methods and compositions for the protection and storage of cells. In particular, the present invention provides methods and compositions for the vacuum-mediated desiccation protection of cells.

The present invention provides methods for desiccation of mammalian cells comprising: providing at least one mammalian cell, and a means for desiccation comprising a vacuum, and exposing the at least one mammalian cell to the means for desiccation, under conditions such that the mammalian cell is desiccated. In some preferred embodiments, the vacuum provides an atmosphere of less than 3% oxygen. In alternative preferred embodiments the at least one mammalian cell is present in a desiccation medium comprising at least one carbohydrate. In further preferred embodiments, the at least one mammalian cell present in a desiccation medium is subjected to thermal shock. In still further preferred embodiments, the carbohydrate is selected from the group consisting of disaccharides and polyols. In particularly preferred embodiments the disaccharide is trehalose. In other embodiments, the mammalian cell is capable of endogenous disaccharide (e.g., trehalose) production. In still other embodiments, the mammalian cell is selected from the group consisting of adherent cells and cells in suspension. In additional embodiments, the mammalian cell is a human cell. In further particularly preferred embodiments, the methods further comprise the step of maintaining the desiccated cell in a vacuum. The present invention also provides desiccated cells produced according to these methods. In some particularly preferred embodiments, the desiccated cell remains viable for more than 3 days, while in other particularly preferred embodiments the desiccated cell remains viable for more than 5 days following desiccation.

The present invention also provides methods for desiccation of cells comprising: providing at least one cell, desiccation medium containing at least one carbohydrate, and means for desiccation; exposing the cell to the desiccation medium to provide a desiccation-ready cell; and exposing the desiccation-ready cell to the means for desiccation, under conditions such that the desiccation-ready cell is desiccated. In some particularly preferred embodiments, the means for desiccation comprises a vacuum. In alternative embodiments, the vacuum provides an atmosphere of less than 3% oxygen. In further preferred embodiments, the at least one cell present in a desiccation medium is subjected to thermal shock. In still further preferred embodiments, the carbohydrate is selected from the group consisting of disaccharides and polyols. In some particularly preferred embodiments the disaccharide is trehalose. In some preferred embodiments, the cell is a mammalian cell. In additional embodiments, the mammalian cell is a human cell. In other embodiments, the cell is capable of endogenous disaccharide (e.g., trehalose) production. In still other embodiments, the cell is selected from the group consisting of adherent cells and cells in suspension. In further particularly preferred embodiments, the methods further comprise the step of maintaining the desiccated cell in a vacuum. The present invention also provides desiccated cells produced according to these methods. In some particularly preferred embodiments, the desiccated cell remains viable for more than 3 days, while in other particularly preferred embodiments the desiccated cell remains viable for more than 5 days following desiccation.

DESCRIPTION OF THE INVENTION

Figure 1:
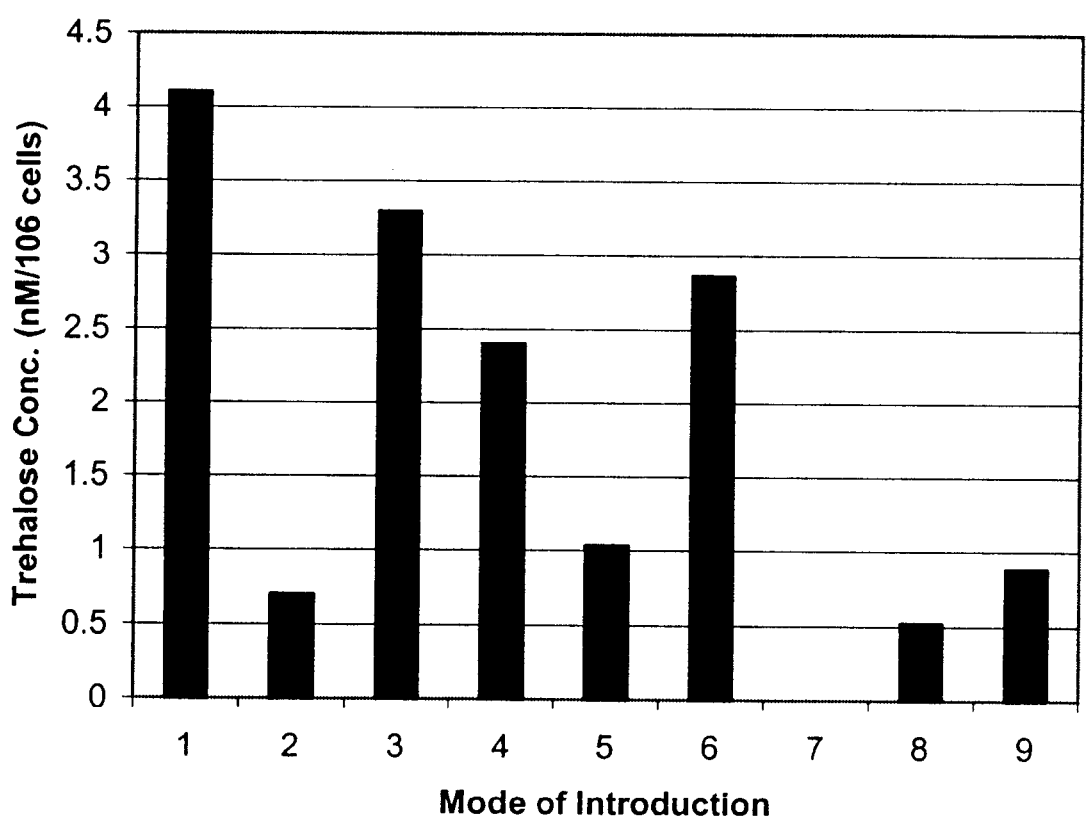
FIG. 1 provides a graph showing the comparison between the modes of trehalose introduction. In this Figure, "1" refers to cells in suspension that were subjected to thermal shock; "2" refers to adherent cells that were subjected to thermal shock; "3" refers to cells in suspension that were subjected to osmotic shock; "4" refers to adherent cells that were subjected to osmotic shock; "5" refers to cells that were incubated for 24 hours; "6" refers to cells that were incubated for 24 hours followed by thermal shock; "7" refers to control cells without exposure to trehalose; "8" refers to cells infected with Ad-ots at an MOI of 300; and "9" refers to cells infected with Ad-ots at an MOI of 400. Adherent cells were at 95% confluence. For cells incubated with trehalose, 50 nM trehalose was used.

The present invention provides methods and compositions for the protection and storage of cells. In particular, the present invention provides methods and compositions for the vacuum-mediated desiccation protection of cells. Indeed, the ability to desiccate and store mammalian cells provided by the present invention greatly simplifies and storage and transportation concerns associated with cells and organs.

Many cells (e.g., seeds, some plants, yeasts, fungal spores, and simple animals) are capable of surviving conditions of complete dehydration to as little as 0.1% water (Crowe et al., Ann. Rev. Physiol., 54:579–599 [1992]). Although an understanding of the mechanism(s) is not necessary in order to practice the present invention, such anhydrobiotic organisms appear capable of tolerating this lack of water due to their ability to synthesize large quantities of certain disaccharides in response to desiccation or high temperature. Trehalose (i.e., a non-reducing disaccharide of glucose) is the most common and perhaps most effective of these disaccharidase. In some anhydrobiotic organisms (e.g., yeast), trehalose is found at about 20% of the dry weight in the desiccated state (See e.g., Crowe et al., supra).

In $E.$ $coli$, trehalose biosynthesis is controlled at the genetic level by the otsA/B locus. This locus encodes trehalose-6-phosphate synthase (otsA). This synthase catalyzes the synthesis of trehalose-6-phosphate from UDP-glucose and glucose-6-phosphate. The locus also encodes trehalose-6-phosphate phosphatase (otsB), which catalyzes the formation of trehalose (Kaasen and Strom, Gene 145:9–15 [1994]). No vertebrate has been shown to be able to synthesize trehalose or to exhibit the degree of desiccation tolerance found in organisms that synthesize trehalose. However, exogenously added trehalose has been used for ex vivo storage and cryopreservation of mammalian organs and cells in the hydrated state (Hirata et al., Surgery 115:102–107 [1994]; and Beattie et al., Diabetes 46:519–523 [1997]).

Although an understanding of the mechanism(s) is not necessary in order to practice the present invention, and indeed, the mechanism by which trehalose mediates desiccation tolerance has not been completely defined, it appears to involve effects on both proteins and lipid membranes. In general, it is believed that trehalose replaces the shell of water around macromolecules, circumventing the damaging effects (e.g., protein denaturation and aggregation) that occur during drying (Crowe et al., Ann. Rev. Physiol., 60:73–103 [1998]). For lipid membranes, it has been shown that trehalose can depress the phase transition temperature such that the membranes remain in the liquid-crystal state even when dry (Leslie et al., Biochim. Biophys. Acta 1192:7–13 [1994]). It is hypothesized that this prevents membrane leakage during rehydration and thereby preserves cellular viability. For proteins, trehalose has been shown to inhibit protein denaturation by exclusion from the protein surface in the hydrated state (Arakawa et al., Cryobiol., 27:401–415 [1990]), inhibit aggregation during heat stress (Singer and Lindquist, Mol. Cell., 1:639–648 [1998]), and preserve the structure of proteins in the dry state (Leslie et al., Biochim. Biophys. Acta 1192:7–13 [1994]; and Leslie et al., Appl. Environ. Microbiol., 61:3592–3597 [1995]), possibly by replacing water molecules that contribute to the maintenance of properly folded protein structures (Allison et al., Arch. Biochem. Biophys., 365:289–298 [1999]). Indeed, the unusual biophysical properties of trehalose have led to its use as a preservative, with successful uses in the food industry, as well as for cryopreservation of human pancreatic islets (Beattie et al., Diabetes 46:519–523 [1997]), enzymes (Colaco et al., Biotechnol., 10:1007–1011 [1992]), DNA products (Uritani et al., J. Biochem. (Tokyo) 117:774–779 [1995]), and liposomes (Crowe et al., Proc. Natl. Acad. Sci. (USA) 84:1537–1540 [1987]).

Some anhydrobiotic organisms use carbohydrates or polyols other than or in addition to trehalose as a desiccation protective agents, including maltose, sucrose, lactose, inositol, and glycerol (Crowe et al., in Leopold (ed.), $Membrane.$ $Metabolism$ $and$ $Dry$ $Organisms$, Comstock Publishing [1986]; and Crowe et al., Biochim. Biophys. Acta 947:367–384 [1988]). For example, sucrose-expressing $E.$ $coli$ exhibit a 10,000-fold increase in survival compared to wild type cells following air drying (Billi et al., Appl. Environ. Microbiol., 66:1680–1684 [2000]). Some carbohydrates and polyols have been used as cryoprotectants for mammalian cells, including glycerol (Renard et al., Cryobiol., 33:311–319 [1996]), dextran (Pellerin-Mendes et al., Cryobiol., 35:173–186 [1997]), and trehalose (Beattie et al., supra). A combination of glycerol and trehalose has also been found to enhance the cryopreservation of mouse sperm (Storey et al., Cryobiol., 37:46–58 [1998]).

However, high degrees of desiccation tolerance, while common in plants and lower animals, is not known to be a common characteristic of higher animals. Indeed, until the development of the present invention, it was unknown whether protection from desiccation could be provided to higher cells by means of intracellular trehalose biosynthesis. During the development of the present invention, the expression of $E.$ $coli$ otsA and otsB in human foreskin fibroblasts by means of an adenovirus vector was utilized, in order to determine whether trehalose expression confers desiccation resistance to cells (e.g., human cells). An adenoviral vector (Ad-GFP) was used in the development of the present invention as this vector provides a means to regulate the level of trehalose in the cell by changing the MOI (multiplicity of infection) of the target cells. Unfortunately, further increases in trehalose expression were not possible with this vector because of the toxicity observed in early experiments. As described in greater detail herein, the infected cells produced trehalose and could be completely dried with maintenance of viability. Unlike the complex trehalose biosynthetic machinery of other organisms, it was surprising that expression of just otsA and ostB was sufficient to produce high levels (about 1 nM trehalose/$10^6$ cells; See, FIG. 1) of trehalose in human cells transfected with $E.$ $coli$ otsA and otsB. However, the optimal MOI for maintenance of viability under desiccation conditions varied somewhat, probably reflecting a balance between the amount of trehalose production and adenoviral infection toxicity.

While this vector resulted in significant levels of intracellular trehalose, it has a number of disadvantages, including the need to constantly produce adenoviral vector, and the fact that adenoviral vectors exhibit significant cytotoxicity, particularly at high multiplicities of infection. Therefore, three alternative methods of trehalose introduction were tested, including osmotic and thermal shock and simple incubation in trehalose media. All of these methods have been reported to mediate efficient entry of proteins into cells (Daw et al., Cryobiol., 10:126–133 [1973]; and Moore et al., Cell 54:777–785 [1988]), but have not been used previously for carbohydrates. Addition of trehalose to adherent cells without osmotic or thermal shock did not result in a significant level of trehalose. However, if the added trehalose was incubated with the cells for a prolonged period of time, the trehalose became tightly associated with the cells, either bound to the surface or internalized. Osmotic shock, while resulting in a substantial increase in cellular trehalose concentration, also caused a large amount of cytotoxicity, so it was abandoned. The condition resulting in the highest level of bound trehalose was found to be thermal shock of cells in suspension (4 nM trehalose/$10^6$ cells) (See, FIG. 1). However, this condition also resulted in a high level of cytotoxicity. Overall, the best condition in terms of a balance between the level of cellular trehalose and cytotoxicity was thermal shock of adherent cells.

While the introduction of trehalose into mammalian cells in culture allowed them to withstand desiccation for up to 5 days, cellular viability decreased rapidly over time. It was hypothesized that this was due to damage to cellular structures that occurred over time in the desiccated state. A strong candidate for the source of that damage was oxygen free radicals. Therefore, the effect of storing the desiccated cells under vacuum was determined. Basinger human primary fibroblasts were plated in 6-well plates and subjected to desiccation in the presence of trehalose introduced by thermal shock or by long-term incubation. Vacuum was then applied by placing the plates inside a plastic bag and using a commercial vacuum sealer ordinarily used for food storage (MagicVac) and the plates were stored for increasing periods of time before being rehydrated by adding tissue culture media. One day after rehydration, viability was measured by trypan blue exclusion. Vacuum was found to have a dramatically positive effect on the retention of cellular viability in the desiccated state (See, FIG. 2). Surprisingly, cells that were desiccated in the absence of trehalose but stored under vacuum retained a high level of viability.

Nonetheless, as discussed in the Examples, there was a gradual decline in cell viability over time in the dehydrated state. The cause of this decline is unknown. Nonetheless, an understanding of the mechanism(s) involved is not necessary in order to use the present invention. Originally, it was thought that this loss in viability reflected a gradual loss of water from incompletely dried cells. However, FTIR spectroscopy data indicated that complete drying occurs very rapidly and that there is no change in water content over time. With the vector described herein, 0.3 to 0.4% of the dry cell weight was obtained as trehalose (assuming a dry weight of 100 pg/cell). Yeast, which withstand prolonged desiccation, contain about 20% trehalose as dry weight (Weimken, Antonie Van Leeuwenhoek 58:209–217 [1990]). Nonetheless, as described herein, the present invention provides novel means to preserve nucleated mammalian cells in a reversibly desiccated form.

In some embodiments, the methods of the present invention involve the use of vacuum to improve the viability of desiccated cells, while in other embodiments, disaccharides such as trehalose are used to improve viability of desiccated cells. In still further embodiments, a combination of vacuum and disaccharides are utilized. In additional embodiments the disaccharide (e.g., trehalose) is used in combination with other compounds (e.g., glycerol). In some particularly preferred embodiments, a combination of 3% glycerol and 50 mM trehalose are used (e.g., in DMEM). In yet other embodiments, the desiccated cells are capable of producing disaccharides and/or other compounds that provide protection from desiccation, while in other embodiments such compounds are added to the cell preservation medium. It is contemplated that longer storage times are achievable, utilizing the methods and compositions of the present invention. It is further contemplated that the present invention will provide welcome advances in storage and transport of mammalian cells to those in the art.

Indeed, using the protocols described herein, in which trehalose and glycerol are introduced into cells by thermal shock and storing the cells under vacuum in the dark, it is possible to maintain cells in the desiccated state with reliable recovery of at least some viable cells for up to eight days. Intermittent successes have also been achieved in recovering viable cells up to two weeks. The reason for the decrease in viability observed over time is not known, but it may be related, at least in part, to the fact that current equipment and methods are unable to completely eliminate air and moisture from the system. However, an understanding of the mechanism(s) is not necessary in order to use the present invention and it is contemplated that the present invention and modifications thereto will find use in long-term storage of viable mammalian cells.

Although an understanding of the mechanism(s) in not necessary in order to use the present invention, one possible mechanism (i.e., in addition to free radical damage) is that exposure to air prior to the final stage of drying eliminates the meniscus effects that could damage cells. However, the hypothesis that free radical induced damage (Calabrese et al., Drugs Exp. Clin. Res., 25:281–287 [1999]) plays important role in limiting the extent and duration of desiccation tolerance was supported by the finding that fluorescent lights had a deleterious effect on the survival of desiccated cells (See, Example 6; and FIG. 4). There is increasing evidence that free radicals play an important role in controlling lifespan, both at the cellular (Ozawa J. Bioenerg. Biomembr., 31:377–390 [1999]; and Pansarasa et al., Free Radic. Biol. Med., 27:617–622 [1999]) and organismal levels (Murakami et al., Ann. NY Acad. Sci., 908:40–49 [2000]). Under ordinary conditions, cells have elaborate mechanisms to prevent and repair damage from free radicals. However, these mechanisms are, for the most part, ineffective in the desiccated state. Once a critical level of damage has occurred in the desiccated state, the subsequently rehydrated cell may be unable to repair itself and in this case, is likely to undergo apoptotic or necrotic cell death.

A significant problem with currently used methods of desiccating cells is the relative lack of control over the rate at which the cells are dried. For example, substantial variations in viability occur from well to well in a single six well plate maintained under identical conditions. The rate of drying can be crudely manipulated by altering the amount of media that remains in the well during the initiation of the desiccation process. Consistently, it was found that a slower rate of drying led to increased viability in the desiccated state. This has been supported by experiments with the lungworm parasite *Muellerius cf. capillaris*, in which a slow rate of drying was found to enhance the viability of desiccated organisms by 10-fold at day 28 when compared with immediate exposure to 0% humidity air (Solomon et al., J. Parasitol., 84:802–805 [1998]). In addition, a recent study reports that high levels of intracellular trehalose conferred tolerance to osmotic stress, but not to desiccation in experiments conducted under laminar air flow (de Castro and Tunnacliffe, FEBS Lett., 487:199–202 [2000]). During the development of the present invention, it was found that under these conditions it was not possible to reversibly desiccate cells. Although an understanding of the mechanism(s) by which a slow rate of desiccation enhances desiccation tolerance is not necessary in order to use the present invention, it is reasonable to speculate that time may be required for cells to adapt to a reduced water content, possibly through the synthesis of new molecules involved in desiccation tolerance. This may be true even when exogenous substances such as trehalose are introduced into the cell.

Prolonged incubation of cells with trehalose resulted in tight association of trehalose with the cells. This was sufficient to enhance desiccation toleration, but it is unknown whether any of the trehalose actually entered the cells. Anhydrobiotic organisms have a trehalose carrier in the plasma membrane which allows for the transport of trehalose to both sides of the membrane (de-Araujo, Braz. J. Med. Biol. Res., 29:873–875 [1996]). Mammalian cells are not known to possess a trehalose transporter, making it likely that the effect of exogenously added trehalose is extracellular. Nonetheless, an understanding of the mechanism(s) is not necessary in order to use the present invention and it is not intended that the present invention be limited to any particular mechanism.

An extremely surprising finding observed during the development of the present invention was that human cells in culture could withstand complete desiccation for substantial lengths of time, even in the absence of trehalose or another exogenously introduced carbohydrate. This indicates that cells from an organism that is not desiccation tolerant have mechanisms that allow them to withstand virtually complete desiccation. The present invention provides means to determine and assess these mechanisms, thereby providing valuable insights into the response of human (and other animal) cells to stress, as well as means to preserve cells.

Definitions

As used herein, the term "desiccation" refers to the drying of an entity of interest. In some embodiments of the present invention, cells are desiccated in the presence of disaccharides. However, in alternative embodiments, cells are desiccated in the absence of exogenously introduced carbohydrate (e.g., trehalose). In particularly preferred embodiments, desiccation is accomplished using a vacuum.

As used herein, the term "thermal shock" refers to exposing cells to highly divergent temperatures. In some embodiments, the cells are exposed to ice-cold temperatures (e.g., approximately 0° C.), and then exposed to a temperature of approximately 35° C. However, it is not intended that the present invention be limited to any particular set of temperatures or times of exposures used in thermal shock protocols. Indeed, those of skill in the art recognize that other temperatures are suitable for use with the present invention.

As used herein, the term "thermotropic phase transition" refers to the phase cells undergo during the transition between the liquid crystalline (i.e., fluid) and gel (i.e., solid) phases. Typically, when the membrane bilayer is in the liquid crystalline state, the lipid molecules are loosely aligned according to their hydrophilic and lipophilic regions, with the lipophilic regions facing each other (i.e., away from the aqueous enviroment). Once the cells pass the phase transition temperature and assume the "solidified" (or "gel") form, the lipid molecules become aligned and more closely packed, limiting the permeability of the bilayer or eliminating the permeability of the bilayer. In the thermotropic phase transition, regions of a loosely packed liquid crystalline phase alternate with regions of a densely packed gel phase. As these phases are not fully compatible, the bilayer molecules form packing irregularities or defects that result in an increase in membrane permeability.

As used herein, the term "transition temperature" ("$T_m$") of a membrane refers to the temperature at which gel-to-fluid melting of membranes occurs. At low temperatures, lipid bilayers are immobilized in a gel state, but increasing the temperature causes the bilayers to "melt" into a more fluid state. The $T_m$ at which this gel-to-fluid melting occurs can be determined by placing the membrane into a sealed chamber (e.g., a calorimeter) in which the uptake of heat is measured as the temperature is increased. The point of maximum heat absorption correponds to the transition temperature. For most membranes, the transition temperature is lower than the normal temperature at which the membrane exists. Thus, in most cases, the bilayers tend to remain in a fluid state. However, as known in the art, $T_m$ values vary significantly for different types of membranes. Membrane fluidity is largely dependent upon three aspects of the membrane's lipid constituents, namely the fatty acid chain length, fatty acid saturation, and steroid content.

Phase transitions may be measured by any suitable method. For example, in some embodiments, phase transitions are measured by changes in membrane $CH_2$ vibrational frequency. In these embodiments, Fourier transform infrared microscopy and temperature-controlled conditions may be used. However, it is not intended that the present invention be limited to any particular method or equipment for measuring and/or monitoring phase transitions of membranes.

As used herein, the term "osmotic shock" refers to the exposure of cells to solutions of differently osmotic pressures. In one embodiment, the cells are placed in a hypertonic solution and then placed in a hypotonic solution. However, it is not intended that the present invention be limited to any particular set of hypotonic and hypertonic solutions, or times of exposure, in osmotic shock protocols. Indeed, those of skill in the art recognize that other solutions and times of exposures are suitable for use with the present invention.

As used herein, the term "osmosis" refers to the net diffusion of water across a selectively permeable membrane that is permeable in both directions to water, but varyingly permeable to solutes, wherein the water diffuses from one solution into another of lower water potential. The "osmotic pressure" of a solution is the pressure which must be exerted upon it to prevent passage of distilled water into it across a semipermeable membrane (i.e., a membrane that is impermeable to all solutes, but is freely permeable to solvent), and is often measured in Pascals (1 Pa=1 Newton/$m^2$).

As used herein, the term "water potential" refers to the net tendency of any system to give up water to its surroundings. As the water potential of pure water at atmospheric pressure is by definition, zero pressure units, any addition of solute to pure water reduces its water potential and makes its value negative. Thus, water movement is from a system with higher (i.e., less negative) water potential to one with lower (i.e., more negative) water potential.

As used herein, the term "hypertonic" refers to a solution with a solute concentration that is higher than that inside cells present in that solution, and therefore causes water to diffuse out of the cells. The term "hypertonic" is a relational term expressing the greater relative solute concentration of one solution compared with another (i.e., the latter is "hypotonic" to the former). A hypertonic solution has a lower water potential than a solution that is hypotonic to it and has a correspondingly greater osmotic pressure.

As used herein, the term "hypotonic" refers to a solution with a solute concentration that is lower than that inside cells present in that solution, and therefore causes water to diffuse into the cells. A hypotonic solution has a lower relative solute concentration (i.e., higher water potential) than another solution.

As used herein, the term "isotonic" refers to solutions that have equal solute concentrations (i.e., as indicated by their osmotic pressure). Separation of isotonic solutions by selectively permeable membranes (e.g., cell membranes), results in no net passage of water in either direction, since the solutions have the same water potential.

As used herein, the term "preservation-enhancing amount" refers to that any amount of a substance that produces a detectable improvement in the retention of cell viability upon desiccation. In some preferred embodiments, the cells are mammalian cells, while in other preferred embodiments, the cells are human cells. In some preferred embodiments, the "preservation-enhancing" substance is at least one disaccharide. In particularly preferred embodiments, the substance comprises trehalose. However, it is not intended that the present invention be limited to trehalose, as other suitable preservation-enhancing substances are described herein.

As used herein, the term "monosaccharide" refers to simple sugars, including molecules containing three carbon atoms (e.g. trioses, such as phosphoglyceraldehyde and phosphoglyceric acid), five carbon atoms (e.g., pentoses, such as ribose [$C_5H_{10}O_5$]) and six carbon atoms (e.g., hexoses, such as glucose, galactose, and fructose [$C_6H_{12}O_6$]). As carbohydrates, the empirical formula of monosaccharides is $C_x(H_{2x}O)_x$, where "x" varies from three to eight. Monosaccharides are carbohydrates that cannot be hydrolyzed to simpler compounds. Some monosaccharides, as well as their amino derivatives, are monomers of biologically important polysaccharides and glycosaminoglycans. The term encompasses aldoses (i.e., compounds with a carbonyl in the form of an aldehyde; e.g., ribose, xylose, arabinose, mannose, etc.), as well as ketoses (i.e., compounds with a carbonyl in the form of a ketone; e.g., ribulose, etc.). It is not intended that the term be limited to any particular type of monosaccharides (e.g., pyranoses, furanoses, etc.).

As used herein, the term "disaccharide" refers to carbohydrates comprised of two monosaccharide groups joined covalently by a glycosidic bond. Disaccharides include, but are not limited to trehalose, lactose, maltose, sucrose, and cellobiose.

As used herein, the term "trisaccharide" refers to carbohydrates comprised of three monosaccharide groups joined covalently by glycosidic bonds.

As used herein, the term "polysaccharide" refers to carbohydrates produced by condensation of many monosaccharide units to form polymers. Polysaccharides include, but are not limited to cellulose, chitin, glycosaminoglycans, starch, amylose, glycogen, amylopectin, and inulin. Typically, an "oligonsaccharide" is a carbohydrate comprised of from two to ten simple sugars linked together.

As used herein, the term "carbohydrate" refers to the class of organic compounds with the approximate empirical formula of $C_x(H_2O)_y$, where y=x (i.e., monosaccharides) or y=x−[n−1] (i.e., di-, oligo-, and polysaccharides), where "n" is the number of monomer units in the molecule. In some compounds, atoms of nitrogen and/or other elements are also present. In addition, the term encompasses polyhydroxyaldehydes and polyhydroxyketones, as well as substances that after hydrolysis, yield polyhydroxyaldehydes and polyhydroxyketones. The term also encompasses all starch and cellulose families, as well as pectin, the seaweed products agar and carrageenan, and natural gums (e.g., water soluble plant products composed of monosaccharide units joined by glycosidic bonds, including but not limited to arabic and tragacanth).

As used herein, the term "polyol" refers to polyhydric alcohols (i.e., one with three or more hydroxyl groups). Polyols with three hydroxl groups (i.e., trihydric) are "glycerols," while those with more than three hydroxyl groups are commonly referred to as "sugar alcohols," with a general formula of $CH_2OH(CHOH)_nCH_2OH$, where "n" may be from 2 to 5. These compounds react with aldehydes and ketones to form acetals and ketals. The term also is used in reference to simple sugars whose carbonyl function have been reduced. Polyols also include, but are not limited to sorbitol and mannitol.

As used herein, the term "mammalian cell" refers to a cell from a mammal. In some preferred embodiments, the cell is a human cell, while in other embodiments, the cells are obtained from domestic animals, laboratory animals, livestock, or companion animals (e.g., rodents, cattle, pigs, sheep, goats, dogs, cats, horses, rabbits, etc.). It is not intended that the present invention be limited to cells from any particular species, as the present invention finds use with any type of mammalian cell. The present invention also finds use with normal cells, cancerous cells, pre-cancerous cells, healthy cells, diseased cells, virus-infected cells, cells from different tissues, cells at different developmental stages such as adult and fetal cells, etc., obtained from any type of animal. In further embodiments, the present invention finds use with mutant cells, including naturally occurring mutant cells, mutant cells which are genetically engineered using knockout technology, insertion, deletion, or replacement, chemically-induced mutant cells, radiation-induced mutant cells, etc., obtained from any type of animal. The present invention further finds use with primary cultured cells, cell line cells, and cells infected with a pathogen such as a virus, bacteria, protozoa, fungus, etc., from any type of animal.

As used herein, the term "cell membrane" refers to cell membrane surrounding mammalian and other cells. In particularly preferred embodiments, the membrane is a phospholipid bilayer membrane. In some embodiments, the membrane is a mammalian cell membrane, while in other embodiments, the membrane is a human cell membrane. Indeed, it is not intended that the present invention be limited to a particular type of cell membrane, as the present invention finds use with a variety of different cell types, and is not limited to any particular type of animal.

As used herein, the term "cell culture" refers to cultures derived from dispersed cells taken from the original tissue, from a primary culture, or from a cell line or cell strain. It is not intended that the present invention be limited to cell cultures from any particular species, as the present invention finds use with any type of animal cell.

As used herein, the term "primary culture" refers to a culture that has been developed from a source host animal and before the first subculture. Thus, a primary culture represents the first in vitro growth of cells. It is not intended that the present invention be limited to primary cultures from any particular species, as the present invention finds use with any type of animal cell.

As used herein, the term "organ culture" refers to three-dimensional cultures of undisaggregated tissues, in which some or all of the histological features of the tissue observed in vivo are observable in vitro. It is not intended that the present invention be limited to organ cultures from any particular species, as the present invention finds use with any type of animal cell.

As used herein, the term "histotypic culture" refers to cells that have been reassociated in a manner such that a three-dimensional tissue-like structure results (e.g., by perfusion and overgrowth of a monolayer, reaggregation in suspension, and infiltration of a three-dimensional matrix). It is not intended that the present invention be limited to cultures from any particular species, as the present invention finds use with any type of animal cell.

As used herein, the term "tissue culture" is a generic term that includes organ cultures, as well as cell cultures. It is not intended that the present invention be limited to tissue cultures from any particular species, as the present invention finds use with any type of animal cell.

As used herein, the term "cell line" refers to cells in a culture after the first subculture. It is not intended that the present invention be limited to cell lines from any particular species, as the present invention finds use with any type of animal cell.

As used herein, the term "cell strain" refers to a cell line derived by selection or cloning. It is not intended that the present invention be limited to cell strains from any particular species, as the present invention finds use with any type of animal cell.

As used herein, the terms "continuous cell line" and "continuous cell strain" refer to cell cultures with the capacity for infinite survival. These cell cultures are sometimes referred to as "established" or "immortal" cultures. It is not intended that the present invention be limited to continuous cell lines or continuous cell strains from any particular species, as the present invention finds use with any type of animal cell.

As used herein, the term "clone" refers to a population of cells derived from one parent cell. It is not intended that the present invention be limited to clones from any particular species, as the present invention finds use with any type of animal cell.

As used herein, the terms "passage" and "subculture" refer to the transfer of cells from one culture vessel to another. Typically, there is a subdivision of the proliferating cell population. Subcultures allow the propagation of cell lines and strains. The "passage number" refers to the number of times that a cell culture has been subcultured.

As used herein, the term "monolayer" refers to a layer of cells that is one cell thick and adhered to a solid substrate.

As used herein, the term "confluent" refers to adherent cells that are in contact with each other, such that there is no substrate that is uncovered by cells.

As used herein, the term "adherent" refers to cells that are anchorage-dependent (i.e., require attachment to a solid substrate or surface for survival or growth), and are attached to a solid substrate.

As used herein, the term "contact inhibition" refers to the inhibition of cell membrane ruffling and cell motility when cells are in complete contact with other adjacent cells (e.g., in a confluent culture). This stage often precedes cessation of cell proliferation, but the two are not necessarily causally related.

As used herein, the term "suspension cultures" refers to cell cultures in which the cells are grown suspended in medium (i.e., these cells do not require a substrate to grow and proliferate).

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. Additionally, transformation refers to cells that have been transformed naturally, usually through genetic mutation or endogenous viral infection.

As used herein, the term "generation number" refers to the number of population doublings that a cell culture has undergone since its initial explantation. Typically, the number is estimated based on the dilutions used at subculture steps.

As used herein, the term "population density" refers to the number of monolayer cells per unit area of substrate. For cells grown in suspension, the term is the "cell concentration."

As used herein, the term "saturation density" refers to the maximum number of cells attainable per centimeter square (for adherent cell cultures) or the maximum number of cells per unit volume (for suspension cultures), under specified culture conditions.

As used herein, the term "seeding efficiency" refers to the percentage of cells in an inoculum which attach to the substrate within a stated time period. This value implies viability or survival, but not necessarily proliferative capacity of the inoculated cells.

As used herein, the term "medium" refers to a mixture of organic salts and other nutrients capable of sustaining cell survival in vitro for at least 24 hours. However, the term also encompasses various medium formats and is intended to be used in its broadest sense herein.

As used herein, the term "growth medium" refers to a medium that is capable of supporting the growth of cell populations in vitro.

As used herein, the term "maintenance medium" refers to a medium that sustains cell survival, but does not foster cell growth and proliferation.

As used herein, the term "desiccation medium" refers to a medium that is suitable for use with cells during the desiccation process and for maintenance of the cells in a desiccated state. In preferred embodiments, desiccation media contain components that help protect the cells from damage that occurs during the desiccation process. In particularly preferred embodiments, desiccation media protect and retain the viability of cells undergoing rehydration, as well as cells that have been rehydrated.

As used herein, the term "balanced salt solution" refers to isotonic solutions of inorganic salts (i.e., buffers) that contains inorganic salts in approximately physiological conditions. In some solutions, glucose is included, although the solutions are usually free of other organic nutrients.

As used herein, the term "chemically defined" refers to medium that is comprised of constituents that are known and characterized.

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "partially purified" refers to the removal of a moderate portion of the contaminants of a sample to the extent that the substance of interest is recognizable by techniques known to those skilled in the art as accounting for a measurable amount of the mixture.

As used herein, the term "substantially purified" refers to molecules, (e.g., nucleic or amino acid sequences) that are removed from their natural environment, isolated or separated, and are at least 60% free, preferably 75% free and more preferably 90% free from other components with which they are naturally associated. Furthermore, an "isolated polynucleotide" is a substantially purified polynucleotide.

"Host," as used herein, refers to a recipient cell or organism.

"Mutant," as used herein, refers to any changes made to a wild-type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

"Wild-type," as used herein, refers to a gene or gene product which has the characteristics of that gene or gene product when isolated from a naturally occurring source. A wild-type gene is that which is most frequently observed in a population and is thus arbitrarily designed the "normal" or "wild-type" form of the gene.

"Staining," as used herein, refers to any number of processes known to those in the field that are used to allow visualization and/or improve visualization of cell component(s) and/or feature(s). Although it is not intended that the present invention be so limited, in some embodiments, trypan blue staining is used.

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

"Amino acid sequence," "polypeptide sequence," peptide sequence, and peptide are used interchangeably herein to refer to a sequence of amino acids.

A "variant" of a nucleotide sequence is defined as a nucleotide sequence which differs from the referenced, parent or wild type nucleotide sequence (e.g., by having one or more deletions, insertions, or substitutions that may be detected using hybridization assays or using DNA sequencing). Included within this definition is the detection of alterations to the genomic sequence of the nucleotide sequence. For example, hybridization assays may be used to detect alterations in: (1) the pattern of restriction enzyme fragments capable of hybridizing to a genomic sequence of the first nucleotide sequence (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The term "portion" when used in reference to a nucleotide sequence refers to fragments of that nucleotide sequence. The fragments may range in size from 5 nucleotide residues to the entire nucleotide sequence minus one nucleic acid residue.

An oligonucleotide sequence which is a "homolog" of a first nucleotide sequence is defined herein as an oligonucleotide sequence which exhibits greater than or equal to 50% identity, and more preferably greater than or equal to 70% identity, to the first nucleotide sequence when sequences having a length of 10 bp or larger are compared.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant molecule containing a desired coding sequence and appropriate nucleic acid sequences necessary for the expression of the operably linked coding sequence in a particular host organism. The sequence may be either single or double stranded. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

"Reporter construct," "reporter gene" and "reporter protein" as used herein, refer to DNA or amino acid sequences, as appropriate, that, when expressed in a host cell or organism, may be detected, measured or quantitated.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "heterologous nucleic acid sequence" (e.g., "heterologous DNA") is used to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined herein as the production of additional copies of a nucleic acid sequence and is generally carried out using polymerase chain reaction technologies well known in the art (see, e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

The terms "reverse transcription polymerase chain reaction" and "RT-PCR" refer to a method for reverse transcription of an RNA sequence to generate a mixture of cDNA sequences, follow ed by increasing the concentration of a desired segment of the transcribe d cDNA sequence s in the mixture without cloning or purification. Typically, RNA is reverse transcribed using a single primer (e.g., an oligo-dT primer) prior to PCR amplification of the desired segment of the transcribed DNA using two primers.

As used herein, t he terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene (i.e. the nucleic acid sequence which encodes a gene product). The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

A "transgenic animal" as used herein refers to an animal that includes a transgene which is inserted into a cell and which becomes integrated into the genome either of somatic and/or germ line cells of the. A "transgene" means a DNA sequence which is partly or entirely heterologous (i.e., not present in nature) to the animal in which it is found, or which is homologous to an endogenous sequence (i.e., a sequence that is found in the animal in nature) and is inserted into the animal's genome at a location which differs from that of the naturally occurring sequence. Transgenic animals which include one or more transgenes are within the scope of this invention.

Experimental

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); BSA (bovine serum albumin); HCl (hydrochloric acid); aa (amino acid); bp (base pair); kb (kilobase pair); kD (kilodaltons); gm (grams); $\mu$g (micrograms); mg (milligrams); ng (nanograms); pg (picograms); $\mu$l (microliters); ml (milliliters); mm (millimeters); nm (nanometers); $\mu$m (micrometer); M (molar); mM (millimolar); $\mu$M (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); HBSS (Hank's balanced salt solution); DMEM (Dulbecco's Modified Eagle's Medium); FBS or FCS (fetal bovine serum); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl) aminomethane); w/v (weight to volume); v/v (volume to volume); MOI (multiplicity of infection); HPLC (high performance liquid chromatography); FTIR (Fourier transform infrared spectroscopy); Flaem Nuova (Flaem Nuova, Brescia, Italy); Kapak (Kapak Corp., Minneapolis, Minn.); Midac (Midac Corp., Irvine, Calif.); Galactic (Galactic Industries, Salem, N.H.); ATCC (American Type Culture Collection, Rockville, Md.); and GIBCO BRL or Gibco BRL (Life Technologies, Inc., Gaithersburg, Md.).

The human embryonic kidney line 293 cells used in the following Examples were obtained from the ATCC (Accession No. CRL1573). The human primary foreskin fibroblast cell line 12F (Guo et al., Nat. Biotechnol., 18:168–171 [2000]) was obtained from Advanced Tissue Sciences. Cells were grown in Dulbecco's Modified Eagle's Medium (DMEM; Gibco BRL), supplemented with 10% fetal bovine serum (FBS; Gibco BRL). Basinger cells (Wang et al., Gene 182:145–150 [1996]; available from various suppliers) were also used in these experiments and grown under the same conditions.

In experiments described here in, trehalose and other compounds were introduced into the cells and/or culture systems using four routes, namely adenoviral introduction (i.e., Ad-OTS), osmotic shock, thermal shock, and simple incubation of the cells in the presence of trehalose (150 mM final concentration) for 24 hours. Cells in suspension as well as adherent cells were used in these various experiments. The reduced metal content D (+) trehalose dihydrate, dextran, mannitol, sorbitol, glycogen and sucrose used in these experiments were purchased from Sigma.

In initial studies conducted during the development of the present invention, a viability assay was used that utilized acridine orange to indicate dead cells and calcein to indicate live cells. In some experiments, the live/dead/viability/cytotoxicity kit (Molecular Probes) was used to differentiate between live and dead cells. However, it was found that this assay system did not always reflect the number of cells that were actually able to grow following desiccation. In later experiments, the same phenomenon was observed with trypan blue staining methods (i.e., the number of cells capable of excluding trypan blue was greater than the number of cells that actually grew). Under some conditions, such as when the cells were dried in the absence of vacuum or trehalose, a substantial number of cells were found to exclude trypan blue immediately after rehydration. However, in almost all cases, these cells did not continue to grow.

Trypan Blue Viability Assay

Trypan blue exclusion was done by adding 10 $\mu$l of 0.4% trypan blue in 0.85% NaCl (Gibco BRL) to 10 $\mu$l of a single cell suspension of trypsinized cells and counting the number of trypan blue positive and negative cells. Colony assays were done by harvesting adherent cells 8–12 hours after rehydration, counting by hemacytometer, and plating either 200 or 300 cells in a 10 cm tissue culture dish. The same number of cells from a non-desiccated control were plated in parallel. Approximately 1 week later, the plates were stained with Giemsa and the colonies were counted.

Colony Viability (Plating Efficiency) Assay

To definitively determine the effect of different desiccation protocols, an assay based on colony formation (i.e., "plating efficiency") was used, as described in the following Examples. In this assay, rehydrated cells were replated at low density and the number of distinct colonies counted. In this way, only rehydrated cells able to undergo cell division were counted as "viable." The pattern of viability determined by trypan blue exclusion and colony assay were the same (e.g., compare FIG. 2A with FIG. 2B), validating the use of trypan blue to measure the effect of various treatments on cell viability. However, the use of the colony assay strengthened the data demonstrating the importance of vacuum in maintaining cellular viability in the desiccated state, as only the cells stored under vacuum retained the ability to grow and form colonies after more than five days of desiccation.

Osmotic Shock Method

The osmotic shock method used in the experiments conducted during the development of the present invention involves the exposure of the cells to hyperosmotic medium (DMEM with 10 mM Hepes, 5% FBS, 50 mM Trehalose, 0.5 M sucrose (final concentration), and 10% PEG-1000 (final concentration)), followed by exposure to hypotonic medium. In this method, $1 \times 10^6$ cells were first placed in suspension, then centrifuged sufficiently to pellet the cells. Then, 200 $\mu$l hypertonic solution were added to the pelleted cells. Following incubation for 8 minutes at 37° C., 20 volumes of hypotonic medium (30 ml HBSS with 20 ml distilled $H_2O$) (Okada and Rechsteiner, Cell 29:33–41 [1982]) were added and the cell suspension was incubated for 4 minutes at 37° C. Then, the shock was terminated by adding DMEM with 10% FBS to the cells. The suspension was then plated in 6-well plates (if prepared for drying experiments) or a trehalose assay was done (if trehalose content was measured). For adherent cells, osmotic shock was conducted using a similar protocol, but with 0.5 ml/well hypertonic or hypotonic solution.

Thermal Shock Method

For thermal shock experiments, trehalose solution (50 mM final concentration) in DMEM and 10% FBS, was added to a pellet of $1 \times 10^6$ cells to produce a cell suspension which was then incubated on ice for 5 minutes, and then for 10 minutes in a 37° C. water bath (Daw et al., Cryobiol., 10:126–133 [1973]; and Moore et al., Cell 54:777–785 [1988]). This cycle was repeated twice. For adherent cells, the cells were plated in 6-well plates and grown to 90–95% confluence prior to thermal shock with 50 mM trehalose as described above. These methods are described in more detail in the following Examples. However, it is not intended that the present invention be limited to any particular temperatures used for thermal shock, as it is known in the art that in some cases, cells can be shocked using different temperatures.

Based on the results obtained, the most effective methods for introduction of trehalose were found to be osmotic shock and thermal shock. As thermal shock is somewhat more rapid and more convenient, it was considered to be the preferred method. In addition, there were some toxic effects observed after long term incubation of cells that were used in osmotic shock experiments. In subsequent experiments conducted later in the development of the present invention, the thermal shock method was used on adherent cells (i.e., on plates).

EXAMPLE 1

Preliminary Vacuum Experiments

In these experiments, 12F cells were placed in two 6-well plates and grown in DMEM, to about 90% confluency. The cells were incubated at approximately 35–37° C., in the presence of 10% $CO_2$. The medium was removed and one of the plates was dried under vacuum (76 cm Hg and 2 to 3% residual oxygen) for 48 hours and another plate was dried without vacuum (i.e., air dried) for the same amount of time, at room temperature. For vacuum storage, the plates were placed into a SealPAK pouch (Kapak), and a vacuum seal was applied using a MagicVac machine (Flaem Nuova). Fresh medium was then added to the wells and the plates were incubated overnight under the conditions indicated above. The next day, the cells were harvested and counted in order to determine the dead/alive ratio by trypan blue discrimination. In the plate dried under vacuum, 61% of the cells were alive, while for the plate dried without vacuum, only 12% of the cells were alive. As described in more detail below, it was also determined that the difference between the vacuum-dried and non-vacuumed dried cell survival was more pronounced with increased drying time.

These preliminary experiments also indicated that the length of exposure to air significantly affects the survival of cells following drying. For example, in experiments in which the cells were directly exposed to air for more than two minutes (i.e., in a hood) after removal of the medium, there were substantially fewer viable cells in the samples after drying, even in the presence of a protectant such as trehalose (20–50 mM). Cytotoxic effects were also observed when trehalose concentrations of more than 50 mM were used.

Another important factor noticed was time involved in drying. After five minutes of direct exposure to air (i.e., in a laminar flow hood), cell samples that were dried under vacuum for as little as one day contained very few, if any, viable cells. After removing the media, 1–1.5 ml media remained, which totally disappeared 8–9 hours after the beginning of the drying period. In addition, cells within centrally located wells tended to have better survival rates than cells within peripherally located wells. For example, cells were typically grown in six-well tissue culture plates prior to desiccation. Large differences in the cell viability in the different wells were consistently observed. Often, cells in the middle three wells in each of the rows exhibited better survival rates, as compared with the cells in the outer wells. In addition, the cells present in the periphery of each well tended to survive better than cells in the center of the wells. Although it is not necessary to understand the mechanism(s) involved in producing these survival differences in order to use the present invention, it is believed that these effects are due to differences in the rate of drying of the cultures, as these results seem to correlate with the areas where residual medium is present early in the drying process.

To achieve a high degree of cell survival following desiccation, gradual desiccation of cells was found to be important. If, after removing the culture medium, the cells were directly exposed to air for more than 2 minutes, the results were quite different, in that there was a substantial decrease in the number of viable cells, if any survived at all. After 5 minutes exposure to air, only a few cells were found to be alive even after a short period of drying.

To decrease the rate of desiccation, experiments were conducted in which a small amount of media (approximately 10 µl) was left in each well. This medium disappeared over 6–8 hours, until the wells appeared completely dry. Early in the development of the present invention, it was observed that the water content of cells dried in this manner was undetectable by FTIR. In contrast, if the medium was completely removed all at once, the survival rate dramatically decreased, with viable cells being infrequently recovered.

EXAMPLE 2

Effect of Trehalose and Vacuum on Desiccation Tolerance of 12F Cells

In this Example, experiments conducted to determine the effect of trehalose and vacuum on desiccation tolerance of 12F cells are described. The 12F cells were prepared at 95% confluence in five 6-well plates. On plates 1 (V+T+) and 3 (V−T+), trehalose (50 mM final concentration) was introduced by thermal shock, as described in above. Medium was then removed from each of the wells, and Plates 1 (V+T+) and 2 (V+T−) were vacuum sealed using the Magic Vac vacuum packaging system (Flaem Nuova) and maintained at room temperature. Plates 3 and 4 were sealed in bags without vacuum and also maintained at room temperature. Three days later, medium (DMEM) was added to the plates, and the plates incubated at 37° C. with 10% $CO_2$ overnight. The next day, the cells were harvested and stained with trypan blue in order to determine the dead/live ratio.

In some experiments, the samples were divided. One portion of the sample was used in the analysis of live/dead cells using trypan blue, as described above, and the second portion was plated into fresh culture media at 25× dilution and incubated until cells grew in the culture. This allowed counting of the live cells based on their "plating efficiency." This was considered to be the best way to estimate the ratio of dead to alive cells.

As indicated herein, those tests in which the dead/live ratio was determined by trypan blue counting, more positive results were obtained than with results of analysis based on plating efficiency. Nonetheless, the presence of trehalose during incubation of the cells resulted in a much higher survival rate, as compared to the controls.

Vacuum exposure and the presence of trehalose were found to have pronounced effects on the survival of the cells. Indeed, the combination of vacuum exposure and trehalose presence had the greatest effect on the short-term survival of the cells. With increasing drying times, the presence of vacuum appears to be more important factor for preservation.

In addition, morphological differences in the cells dried with and without trehalose were observed. Dead cells dried in the presence of trehalose were found to appear very similar in size and shape to live cells, while dead cells dried without trehalose were shredded, detached and contained a lot of debris. Thus, there are observable differences in the cells exposed to trehalose, compared to those that have not been exposed to the sugar. Although an understanding the mechanism involved is not necessary in order to practice the present invention, it is possible that in the presence of trehalose, some of the dead cells are impermeable to the stain and are therefore counted as "live," resulting in the differences in plating efficiencies and live count values.

EXAMPLE 3

Development and Characterization of an Adenoviral Vector Expressing otsA and otsB In these experiments, the CMV-OTS expression cassette was inserted into an adenoviral vector (designated "Ad-OTS"), in order to determine whether a wide variety of cell types could express trehalose. As a control, an adenoviral vector expressing GFP (Ad-GFP) was used (Leibowitz et al., Diabetes 48:745–753 [1999]).

To develop a mammalian expression vector for otsA and otsB, a 1.4 kb fragment encoding otsA (trehalose-6-phosphate synthase) and a 0.8 kb fragment encoding otsB (trehalose-6-phosphate phosphatase) were amplified from *E. Coli* DH5α cells.

The primers used in these PCR reactions were: 5'-CCGCTCGAGCACCACCATGACAGAACCGTTAACCGAAACC-3' (SEQ ID NO: 1) and 5'-CGGAATTCTTAGATACTACGACTAAACGAC-3' (SEQ ID NO:2) for otsB, and 5'-TGCTCTAGACCACCATGAGTCGTTTAGTCGTAGTATCTAAC-3' (SEQ ID NO:3) and 5'-AGCGGCCGCCTACGCAAGCTTTGGAAAGGTAGC-3' (SEQ ID NO:4) for otsA. To increase the translational efficiency in eukaryotic cells, a valine codon was replaced by a methionine codon at the 5' end of otsA, and a Kozak consensus sequence was introduced 5' of the start codon of both otsA and otsB. A dicistronic unit comprising these two genes was created in the cloning vector pGEM-7z(+) (Promega) using the 732 bp poliovirus internal ribosomal entry sequence (Pelletier and Sonenberg, Nature 334:320–225 [1988]), as known in the art. The insert was sequenced to eliminate the possibility of mutations introduced by the PCR. This "otsB-PO-otsA" fragment was subcloned into a CMV expression vector plasmid pCMV-MNK as known in the art, to generate the plasmid pCMV-OTS.

A BstXI-BstXI restriction fragment from pCMV-OTS extending from 5' of the CMV promoter to 3' of the polyadenylation sequence was subcloned into the EcoRV site of the adenoviral vector shuttle plasmid pXCX2 (Spessot et al., Virol., 168:378–387 [1987]), as known in the art. The resulting plasmid, pXCX2/CMV-OTS, was used along with the adenovirus plasmid pJM17, to generate recombinant adenovirus (Ad-OTS), as known in the art (See e.g., Berkner, Curr. Top. Microbiol. Immunol., 158:39–66 [1991]). Recombinant adenovirus expressing the GFP gene under control of the chicken actin promoter (Ad-GFP; Leibowitz et al., Diabetes 48:745–753 [1999]) was used as a control.

These vectors were used to infect 12F human primary foreskin fibroblasts. In these transfections, 6-well plates were plated with $3 \times 10^5$ cells/well. The cells were infected six hours later, with Ad-OTS or Ad-GPF at MOIs ranging from 200 to 800. Drying was achieved by complete removal of the tissue culture medium 72 hours after infection, followed by sealing the plates in plastic bags that were then stored at room temperature. To determine whether the cells retained viability, fresh tissue culture medium was added after various intervals in the dry state and the viability of the rehydrated cells was determined by calcein AM/ethidium bromide staining. After 48 hours of incubation at 37° C. in 10% $CO_2$, the cells were harvested, trehalose assays performed, and the samples subjected to HPLC analysis. Trehalose was detected in 12F cells infected with Ad-OTS, but not in cells infected with Ad-GFP. There was a direct relationship between the amount of trehalose production and the MOI. The maximal level of trehalose production ranged from 1 to 1.5 nM/$10^6$ cells at an MOI of 1000 PFU/cells, the highest MOI tested. The trehalose concentrations were determined as described in Example 6.

After 24 hours in the dried state, the 12F cells infected with Ad/CMV/OTS were found to have retained a high degree of viability, as indicated by green, but not orange staining. In contrast, the cells infected with Ad-GFP were completely dead, as indicated by the absence of green and the presence of orange staining. However, the viability of Ad-OTS-infected cells was found to decrease as the length of time in the desiccated state increased. There was significant variability in the optimal MOI for retention of maximal viability (indicated by a range of 200 to 800). This may reflect differences in the infection efficiency, depending upon the state of the cells at the time of infection, combined with a balance between maximizing trehalose production and minimizing toxicity from adenoviral infection. However, an understanding of the mechanism(s) is not necessary in order to use the present invention.

EXAMPLE 4

Expression of Trehalose in Mammalian Cells

In this Example, experiments that were conducted in order to determine whether trehalose could be expressed by 293 cells transfected at full confluence (~100%) with Ad-OTS are described.

Forty-eight hours post-transfection, the cells were extracted and analyzed (using HPLC) for the presence of trehalose. The test and control cells were pelleted, resuspended in 1 ml distilled water, lysed by freeze-thaw, and centrifuged to remove debris. Each sample was then distributed into two tubes. In each tube, 100 μl citric acid buffer (pH 5.7), were added. For trehalose digestion, 0.03 units of dialyzed trehalase were added and the samples were incubated at 37° C. for 2 hours, followed by boiling, to inactivate the trehalase. For undigested samples, the same volume of 25 mM potassium phosphate was added, instead of trehalase. The HPLC standard was 5 nM trehalose in water. This same solution was used as a digestion control for trehalase-treated samples.

Following centrifugation, the supernatants were loaded onto Micro Bio-Spin chromatography columns (Bio-Rad) with mixed bed analytical grade ion exchange resin to remove charged molecules (trehalose is a neutral sugar). The flow-through was dried using a Speed Vacuum Concentrator (Savant). Then, 200 µl distilled water was added to each sample for HPLC analysis.

HPLC was done using a Dionex system DX-500, with AS3500 and a CarboPac MA1 column (4×25 mm) (Dionex), at a flow rate of 0.4 ml/min, at 8° C. An ED 40 electrochemical detector was used to quantitate the amount of trehalose. Water and 1 M NaOH were used as the eluent. In the first 40 minutes, 200 mM NaOH was used. Subsequently, the NaOH concentration was linearly increased from 200 mM to 660 mM over 25 minutes.

A large peak that was not present in untransfected cells was detected at about 28 minutes retention time. To confirm that this peak represented trehalose, the cell extract was incubated with trehalose, resulting in the almost complete disappearance of the putative trehalose peak. These data definitively identified the peak observed at about 28 minutes as trehalose.

EXAMPLE 5

Trehalose Expression in Mammalian Cells is Non-Toxic

In this Example, experiments conducted to determine whether trehalose production is toxic to mammalian cells are described. In these experiments, 12F cells were seeded at a density of $3 \times 10^5$ cells per well in a 6-well plate. The cells were infected 8 hours later with Ad-OTS at MOIs ranging from 100 to 1000, and incubated at 37° C. in 10% $CO_2$. One day after infection, the medium (DMEM with 10% FCS) was replaced with fresh medium and the cultures were reincubated for another 24 hours under the same incubation conditions as above. Adherent cells were then harvested and stained with calcein AM (CAM) to visualize live cells and ethidium homodimer-1 (EthD-1) to visualize dead cells (Live/Dead/Viability/Cytoxicity kit; Molecular Probes).

Cells simultaneously exhibiting green granular perinuclear staining and red nuclear staining were interpreted as being in the process of dying and were counted as dead. At high MOIs, toxicity was observed in cells infected with both Ad-OTS and Ad-GFP vectors, as is commonly observed with adenoviral vectors. No detectable differences between the two viruses were observed, demonstrating that trehalose production is non-toxic for mammalian cells.

EXAMPLE 6

Efficacy of Trehalose Introduction into Cells

In this Example, the efficacy of different methods for trehalose introduction into 12F cells was compared. In these experiments, Ad-OTS, osmotic shock, thermal shock, incubation in high trehalose concentrations, and combinations of these methods were used and compared. The effects of vacuum and trehalose on desiccation tolerance, as well as the effects of trehalose concentration, fluorescent light, confluence and temperature were investigated.

I. Adherent and Suspension Cultures Tested Using Osmotic and Thermal Shock Methods In these experiments, adherent and suspension cultures of 12F and Basinger human fibroblast cells were used. The cells were trypsinized, pelleted, and resuspended into DMEM containing 10% FBS and 50 mM (final concentration) trehalose. For the adherent cells, eight dishes of cells were grown as described above to about 50% confluence, and then two of them were infected at 300 or 400 MOI with Ad-OTS. Following overnight incubation at 37° C. with 10% $CO_2$, trehalose was added to the medium of one of the cultures and this trehalose-treated culture was incubated at 37° C. (with 10% $CO_2$) overnight. The following day, when the cultures reached approximately 90–95% confluence, osmotic and thermal shock procedures were used for both the adherent and suspension cultures. After these shock procedures, samples treated with trehalose were washed repeatedly (4–5 times) with PBS prior to assaying for cell-associated trehalose. Trehalose assays were then immediately performed on all of the samples and the trehalose level estimated by HPLC (See, FIG. 1). The thermal shock method was found to provide the highest level of trehalose introduction into the cells, although the osmotic shock method also provided good levels of trehalose introduction. However, the osmotic shock method resulted in cells that became slower growing than cells that were treated with thermal shock.

FIG. 1 provides the results for adherent and suspension cultures treated using either osmotic or thermal shock. As indicated in FIG. 1, addition of trehalose to adherent cells without osmotic shock or thermal shock did not result in a significant level of trehalose. However, when the added trehalose was incubated with the cells for a prolonged period of time (e.g., 24 hours, as shown in FIG. 1), the trehalose became tightly associated with the cells (either bound to the surface or internalized). Osmotic shock, while resulting in a substantial increase in cellular trehalose concentrations, also caused a large amount of cytotoxicity, as indicated in FIG. 1. Thus, this method was abandoned in subsequent experiments. As indicated in FIG. 1, the treatment that resulted in the highest level of bound trehalose was thermal shock of cells in suspension (e.g., approximately 4 nM trehalose/$10^6$ cells). However, these conditions also resulted in high toxicity levels. Overall, the best conditions, in terms of a balance between the level of cellular trehalose and cytotoxicity was thermal shock of adherent cells and incubation for 12 or 24 hours.

II. Effect of Vacuum Exposure on Desiccated Cells

While the introduction of trehalose into mammalian cells in culture allowed the cells to withstand desiccation for up to five (5) days, cellular viability was found to rapidly decrease over time. It was hypothesized that this loss in viability was due to cell structure damage that occurred over time when the cells were in the desiccated state. A strong candidate for the source of that damage was the presence of oxygen free radicals.

Thus, to determine the effects of vacuum on desiccation tolerance of cells, two 6-well plates of 12F cells at approximately 95% confluency were dried for three days in plastic bags, with one plate dried under vacuum (76 cm Hg and 2–3% residual oxygen), and the second plate dried without exposure to a vacuum. On the third day of incubation under these conditions, medium (DMEM with 10% FBS) was added to the plates, and the plates were incubated overnight at 37° C., in the presence of 10% $CO_2$. Following this overnight incubation, the cells were harvested by trypsinization and counted. In some experiments, FACS was used to determine the ratio of live and dead cells, while in other experiments, trypan blue staining was used to determine this ratio.

Figure 2:
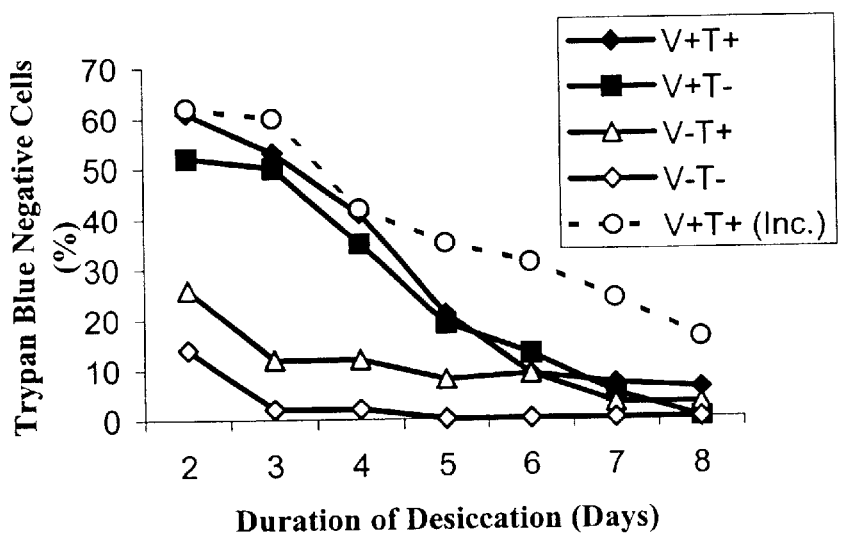
FIG. 2 provides a graph showing the effect of vacuum on desiccation tolerance. Panel A shows the results for the trypan blue exclusion method, while Panel B shows the results for the colony assay. In these experiments, cells were desiccated by removal of all medium followed by storage with (V+) or without (V−) vacuum. Trehalose was introduced by thermal shock or by incubation for 24 hours with 50 mM trehalose (i.e., "Inc." in this Figure). The initial viability prior to desiccation was 93%.
Figure 2:
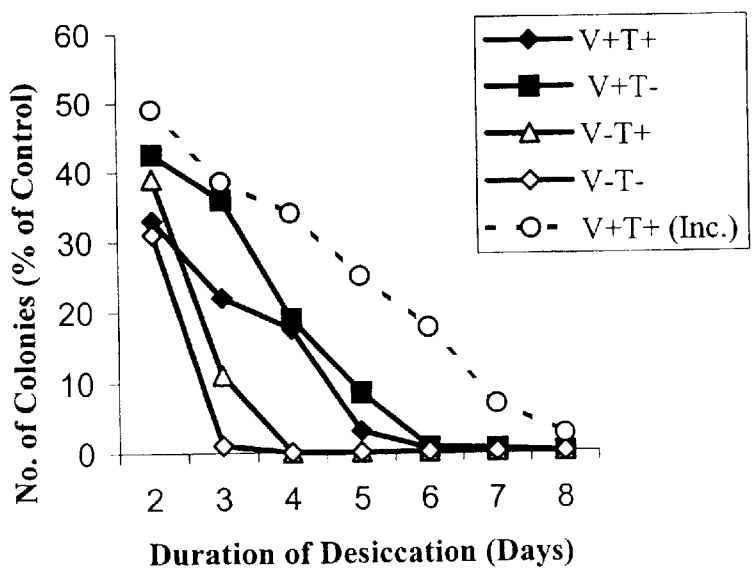

As indicated in FIG. 2, applying vacuum during desiccation time had a dramatic and positive effect on the level of cell survival in the desiccated state. The results for multiple experiments indicated that the cells dried under vacuum had a constant survival rate of between 32% and 40%, while the cells dried without vacuum had a survival rate of less than 4%. In addition, it was observed that passage of cells determined to be "live" has an effect on the survival of the cell culture. For example, some cells dried without exposure to vacuum for less than three days appeared to be "alive," but were unable to grow upon passage into fresh culture medium. Surprisingly, cells that were desiccated in the absence of trehalose, but stored under a vacuum, retained a high level of viability, although the best conditions remained a combination of preincubation with trehalose, thermal shock to promote intracellular entry of trehalose and vacuum. To determine the optimal concentration of trehalose that would result in the highest degree of desiccation tolerance with minimum cytotoxicity, a dose response experiment was conducted. The results indicated that the optimal concentration of trehalose for desiccation tolerance is 50 mM (See, FIG. 3 and below).

III. Effect of Trehalose Concentration on Desiccation Tolerance

Figure 3:
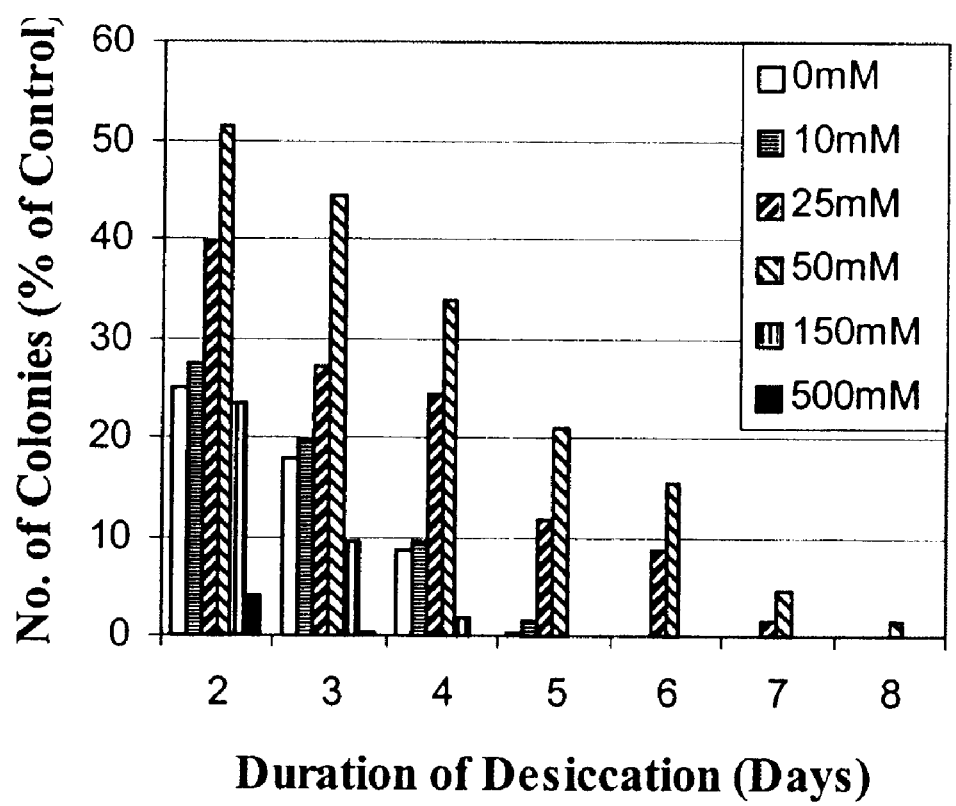
FIG. 3 provides a graph showing the effects of trehalose concentration on desiccation tolerance of adherent cells.

In these experiments, the effects of trehalose concentration on desiccation tolerance were determined. Adherent Basinger cells were prepared in 6-well plates, and incubated at 37° C., with 10% $CO_2$. When the cells reached 65–70% confluence, the cells were incubated with varying concentrations of trehalose (10 mM, 25 mM, 50 mM, 150 mM, and 500 mM) for 24 hours. The cells were exposed to thermal shock and desiccated as described above. These results indicated that over time, the viability of the cells decreases. Nonetheless, as indicated in FIG. 3, the experiments indicate that the optimal trehalose concentration for the highest rate of cell survival (i.e., with no toxicity and the highest number of colonies) was found to be 50 mM, with concentrations above 150 mM resulting in obvious cytotoxicity.

IV. Effect of Fluorescence on Desiccation Tolerance

Because of the concern that free radical-induced damage may play a substantial role in limiting the length of time that cells can withstand desiccation, the effects of fluorescent lighting on desiccation tolerance were investigated. In initial experiments conducted during the development of the present invention, desiccated cells were left in the open on laboratory benches under fluorescent lights for 3 or 5 days.

Light from various sources (e.g., fluorescent lamps, sun lamps, and the sun) has been recently shown to be toxic and mutagenic to cells. For example, exposure to fluorescent light results in the generation of free radicals within hamster and human cells, generating oxidative DNA lesions and single-strand breaks (See e.g., Erickson et al., Biochim. Biophys. Acta 610:105–115 [1980]; Lipinski et al., Nucleic Acids Res., 27:3153–3158 [1999]; and Gannt et al., Proc. Natl. Acad. Sci. USA 75:3809–3812 [1978]).

Twelve 6-well plates (divided into 2 groups) were grown to 95% confluence and dried under vacuum. Half of the plates were maintained under fluorescent lights on the laboratory benchtop, while the other six were wrapped in black paper. On day 3 of desiccation, medium was added to all of the plates. For the first group, one day after rehydration (i.e., day 4), the cells were harvested and the viability determined by trypan blue exclusion. For the second group, medium was added to the 3 plates on day 5. One day after rehydration (i.e., day 6), the cells were harvested and the viability determined by trypan blue exclusion.

Figure 4:
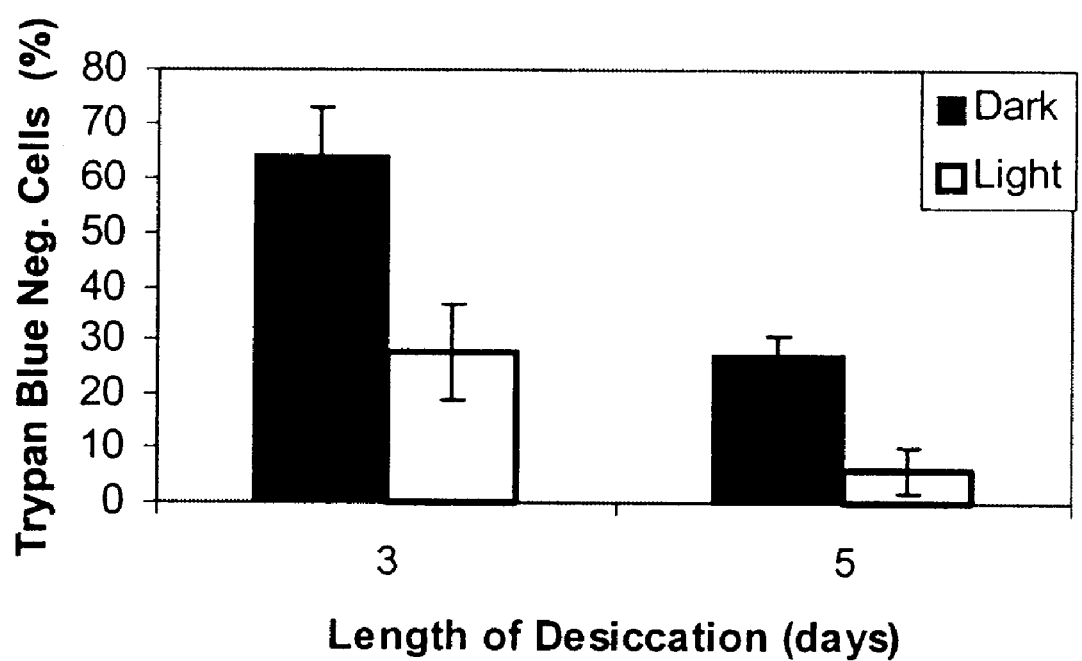
FIG. 4 provides a graph showing the effect of light on desiccation tolerance.

Desiccated cells maintained in the dark were found to have a much greater viability rate than those maintained under the fluorescent lights, as indicated by FIG. 4. These results are consistent with the hypothesis that free radical-induced damage from fluorescent lights is at least partially responsible for the observed decrease in the length of time that cells can be maintained in the desiccated state and retain their viability.

V. Effect of Confluence on Desiccation Tolerance

As indicated previously, to optimize the ability of cultured cells to withstand desiccation, a number of factors were taken into consideration, including the effects of confluence and temperature. In these experiments, 6 dishes (10 cm) containing 12F cells were prepared at different confluency levels (15%, 30%, 50%, 70%, 85%, and 100%) in DMEM. After about 8 hours of incubation at 37° C., in the presence of 10% $CO_2$, when the cells appeared to be well-shaped and attached, the media were removed and all 6 dishes were dried for 2 or 4 days. On day 2 or 4, media were added to the dishes and following overnight incubation at 37° C. with of 10% $CO_2$, the cells were counted (i.e., the viability was determined by trypan blue exclusion). For cultures dried for 2 days, no substantial differences in cell survival were observed for the various confluency levels. However, for the cultures dried for 4 days, the cell survival varied depending upon the confluency levels. The following Table shows the results for the cultures dried for 4 days.

TABLE 1

Cell Survival Rates at Various Confluency Levels

| | Percent Confluency | | | | | |
|---|---|---|---|---|---|---|
| | 15 | 30 | 50 | 70 | 85 | 100 |
| Cell Survival | 11% | 19% | 28% | 32% | 44% | 26% |

Figure 5:
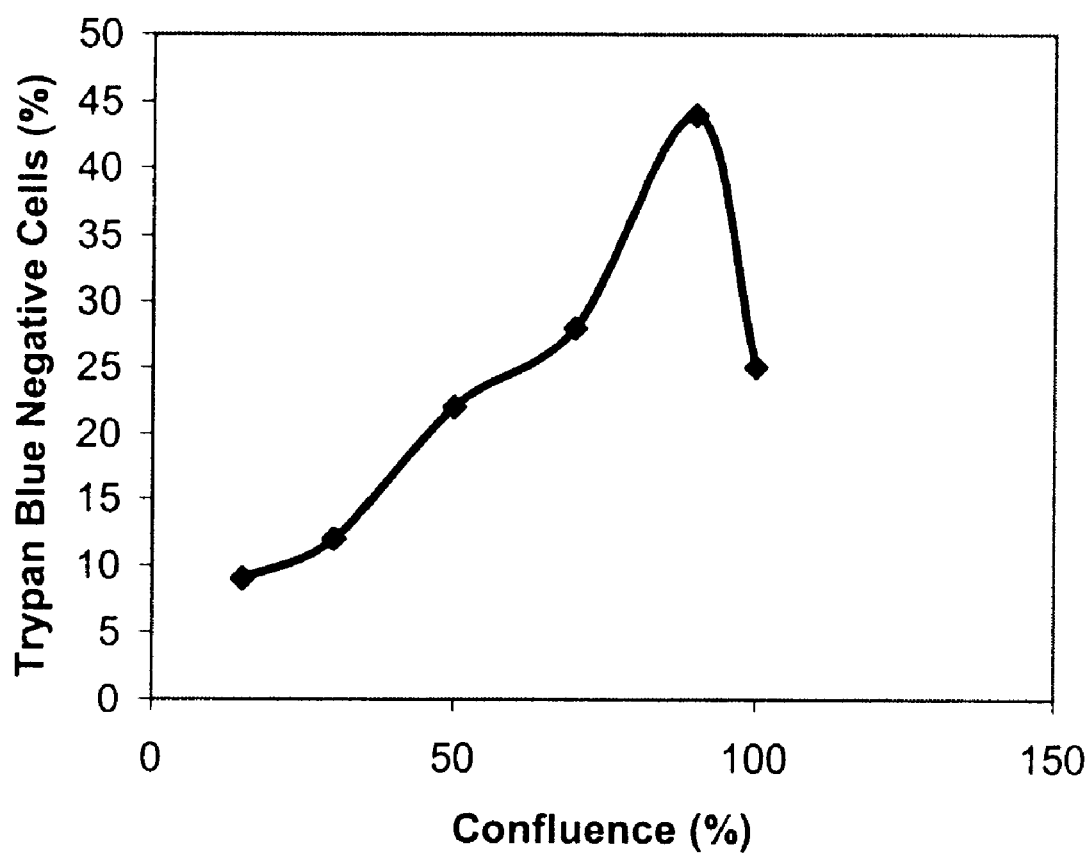
FIG. 5 provides a graph showing the effects of culture confluence on desiccation tolerance.

Thus, for cultures at less than 50% and at 100% confluency, adverse effects upon drying were observed. As indicated in the above Table and FIG. 5, optimal desiccation tolerance was observed at relatively high cell density. However, when the cells were too crowded, desiccation tolerance decreased, perhaps as a result of the general decrease in viability that occurs when cells in monolayers become too densely packed together.

VI. Effects of Temperature on Desiccation Tolerance

In these experiments, the effects of temperature and drying on cell survival were investigated. In addition, the effects of the presence of trehalose on cell survival under different conditions of temperature and drying were investigated. Ten 6-well plates of 12F cells were prepared at about 90–95 confluence. The day prior to the beginning of the drying period, five plates were exposed to thermal shock to introduce trehalose into the cells (as described above). On the first day of the drying period, all of the plates were dried, and the plates were incubated in pairs (i.e., one with trehalose and one without trehalose) at −70° C., −20° C., room temperature, and 37° C., for 4 days.

Figure 6:
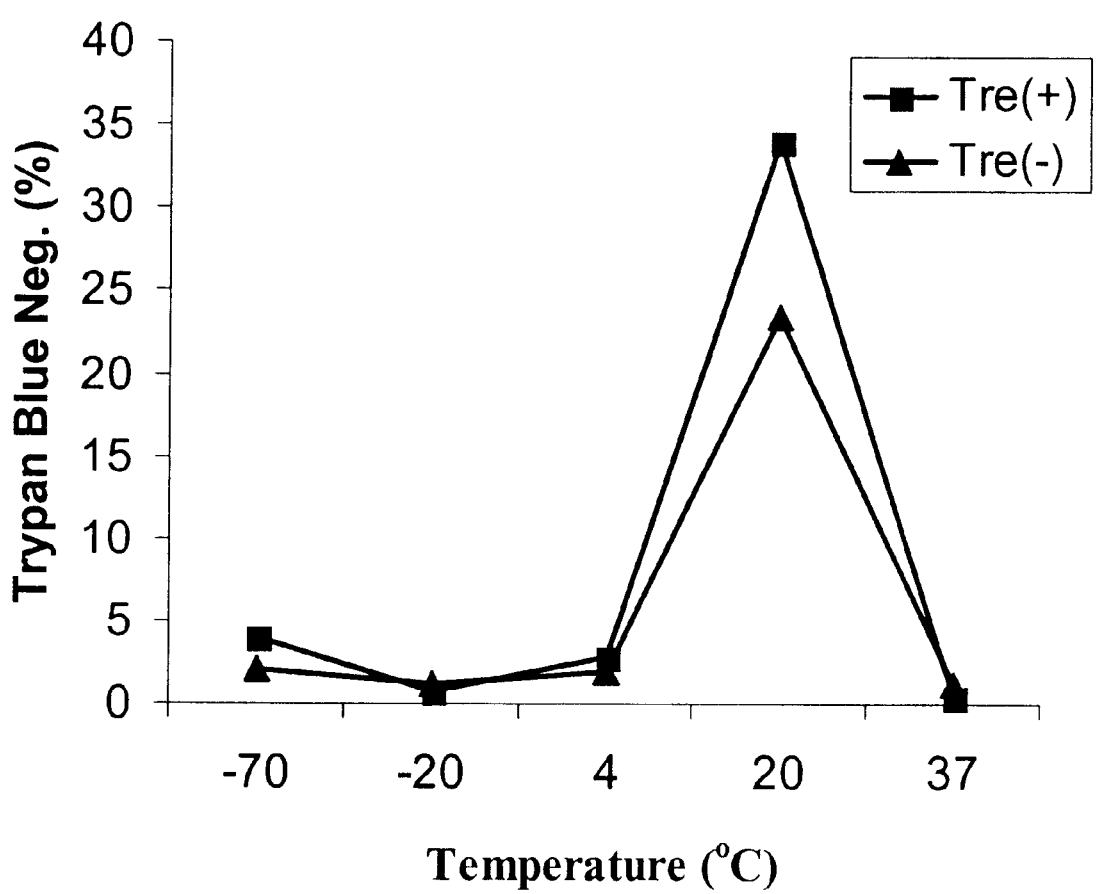
FIG. 6 provides a graph showing the relationship of temperature and desiccation survival for cells with and without trehalose.

In additional experiments to determine the effect of temperature on the ability of cells to withstand desiccation, 6-well plates with 12F cells were prepared at approximately 90% confluence, dried under vacuum at room temperature as described above, and stored at −70° C., −20° C., 4° C., 20° C., and 37° C. for 3 days. In these experiments, two plates were used, one included trehalose (50 mM) introduced into the cells using thermal shock, as described above. The second plate did not include trehalose. The cells were then rehydrated and the viability was determined by trypan blue exclusion. The results are shown in FIG. 6. As indicated in this graph, the temperature at which the cells were stored when desiccated had a dramatic effect on cell survival. The optimum survival temperature was determined to be about 20° C. (i.e., approximately room temperature). At the other temperatures examined, there were almost no viable cells remaining, as determined by trypan blue exclusion, and none were able to grow and form colonies (results not shown). In these experiments, the presence ("Tre(+)")/absence ("Tre(-)") of trehalose appeared to have no impact on the optimum temperature.

The results indicated that except for the cultures incubated at room temperature, no cells survived the drying period. Even the cells dried in the presence of trehalose and incubated at −70° C. were found to be non-viable, with about 4% of the cells appearing to be "live" (using FACS), and showing no growth upon subsequent plating. For the cells incubated at room temperature in the presence of trehalose, the survival rate was found to be very high. No colonies were ever grown from cells maintained in the desiccated state at temperatures other than approximately 20° C. The results are presented in the following Table and FIG. 6.

TABLE 2

Cell Survival

| | Storage Temperature | | | | |
|---|---|---|---|---|---|
| | −70° C. | −20° C. | 4° C. | RT* | 37° C. |
| With Trehalose | 4% | 0.7% | 2.8% | 34% | 0.4% |
| Without Trehalose | 2.1% | 1.2% | 1.9% | 23% | 1.1% |

RT = Room Temperature

The cell morphologies of these cultures also appeared different, with the cells dried without trehalose appearing shapeless and not well attached, while the cells dried with trehalose appeared to be more "normal."

EXAMPLE 7

Effects of Various Disaccharides and Polyols on Drying Tolerance

In these experiments, the effects of various disaccharides and polyols on the drying tolerance of Basinger human fibroblasts were investigated. Although an understanding of the mechanism(s) is not necessary in order to practice the present invention, it appears that in some anhydrobiotic organisms, other disaccharides appear to provide the same protective properties as trehalose. Thus, some anhydrobiotic organisms are able to use carbohydrates other than or in addition to trehalose as a desiccation protectant (See e.g., Crowe et al., Biochim. Biophys. Acta 947:367–384 [1988]; and Crowe, "Stabilization of Membranes in Anhydrobiotic Organisms," in Leopold (ed.), *Metabolism and Dry Organisms*, Comstock Publishing [1986], pages 188–209). Polyols have two distinct functions in anhydrobiotic organisms. They serve as water substitutes, by forming hydrogen-bonded interactions with polar or charged entities of the cell (Hallsworth, Lett. Appl. Microbiol., 18:8–11 [1994]; and Hallsworth and Magan, Microbiol., 141:1109–1115 [1995]) and provide a protein-stabilizing structure at low water conditions (i.e., low water content).

To determine whether any of these molecules have properties that would allow them to substitute for trehalose in promoting desiccation tolerance in mammalian cells, a number of carbohydrates and polyols were systematically studied. Each was tested initially to determine the maximum concentration at which they could be used without causing cytotoxicity. The ability of the different molecules to mediate desiccation tolerance was then tested at the optimal concentration for each. Because of its efficacy with trehalose, the protocol used for desiccation was incubation with the carbohydrate or polyol for 12 hours followed by air drying and storage in the dark under vacuum (See, FIG. 7).

Figure 7:
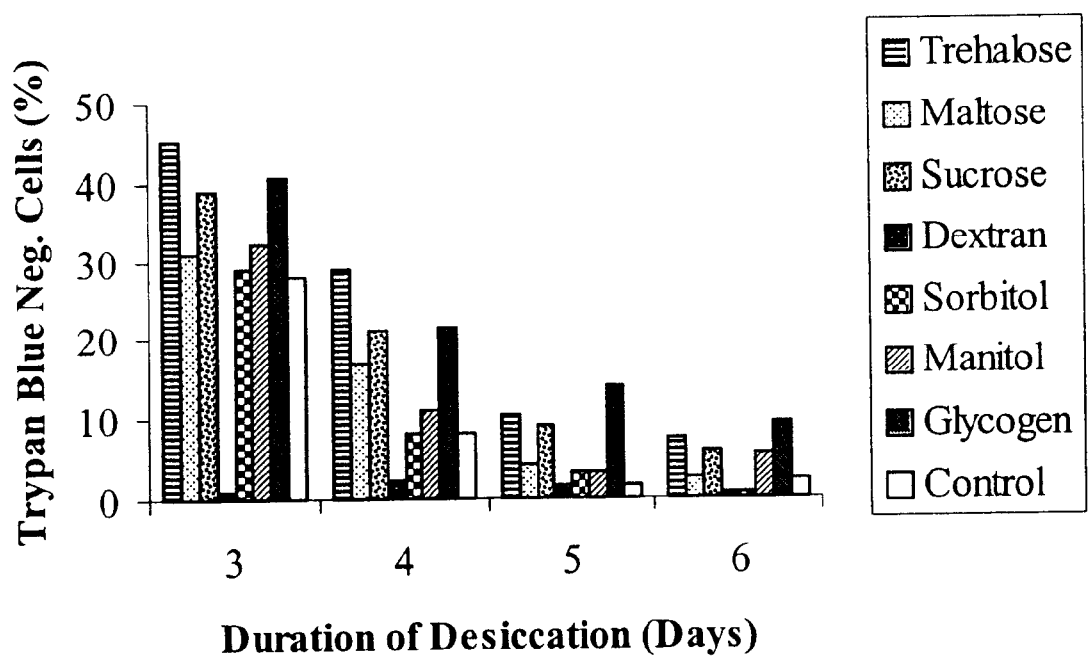
FIG. 7 provides a graph showing the effects of polyols and disaccharides on desiccation tolerance.

Thus, in these experiments, Basinger fibroblast cells were tested in long term desiccation experiments (i.e., longer than 5 days of drying). In these experiments, Basinger cells at approximately 75% confluence were exposed to a polyol or disaccharide for 12 hours prior to removal of medium and desiccation under vacuum. Thermal shock was used to introduce the disaccharides or polyols into the cells to produce equal concentrations final of 50 mM in the cultures (with equal numbers of cells). In these experiments, trehalose, maltose and sucrose were used at 50 mM, while dextran, sorbitol, mannitol, and glycogen were used at a final concentration of 5%. The following Table shows the results obtained, as well as the disaccharides and polyols tested for cells dried for 3, 4, 5, or 6 days and the indicated concentration of test disaccharide or polyol. FIG. 7 also provides a graphic representation of the results for various test disaccharides and polyols.

The results from repeat experiments with thermal shock treatment using trehalose, maltose and sucrose are shown in the following Table.

TABLE 3

Cell Survival with Various Disaccharides and Polyols

| Test Disaccharide/ Polyol | Cell Culture Survival (%) | | | |
|---|---|---|---|---|
| | Day 3 | Day 4 | Day 5 | Day 6 |
| Trehalose (50 mM) | 45 | 38 | 12 | 10.5 |
| Maltose (50 mM) | 31 | 17 | 4.2 | 2.5 |
| Sucrose (50 mM) | 39 | 28 | 9.1 | 7.2 |
| Dextran (10% solution) | 0.9 | 2.4 | 1.7 | 0.8 |
| Glycol (10% solution) | 2.6 | 4.8 | 0.7 | 3.1 |
| Sorbitol (10% solution) | 29 | 8 | 3.1 | 0.8 |
| Mannitol (10% solution) | 32 | 11 | 3.1 | 5.4 |
| Glycogen (10% solution) | 40.6 | 21.5 | 14 | 9.5 |
| Control Cells | 4.4 | 3.1 | 1.5 | 2.3 |

The results obtained in these experiments indicate that sucrose was as effective as trehalose in protecting the viability of the cells. Indeed, sucrose and glycogen were almost equally as effective in providing drying tolerance. However, it was not possible to maintain the sucrose-treated cells counted as "live" in a monolayer culture. These "live" cells floated in the medium and did not grow. Dextran and glycerol were found to be toxic, as the cell survival rate was very low, at concentrations of 5% and more, and the cells did not grow upon passage. At concentrations above 4% (final) glycerol, the solutions were found to have a long-term cytotoxic effect. Thus, 3% glycerol was determined to be the optimum concentration. Glycogen was found to not be toxic at 10% to 15% concentration, to the cells, but toxic if the cells are exposed to very high concentrations of the compound for a long time period. Thus, in these experiments, a 10% solution of glycogen was used. In sum, aside from dextran, which was completely ineffective in preserving cellular morphology or viability, the results with all of the carbohydrates and polyols were qualitatively similar. Each was able to mediate preservation of membrane integrity as measured by trypan blue exclusion (See, FIG. 7). However, none except trehalose and glycerol was able to maintain cellular viability as determined by the ability of the cells to form colonies following rehydration (not shown). Therefore, glycerol was studied further by itself and in combination with trehalose, as described in Example 8.

EXAMPLE 8

Effects of Trehalose in Combination with Other Sugars Compared with Trehalose Alone In this Example, experiments to observe the effects of various combinations of sugars on cell viability are described. The results obtained for these combinations were then compared with the results obtained for trehalose alone. The combinations used were trehalose with glycerol, and trehalose with mannitol. Controls were also tested with no sugars, and trehalose alone. In these experiments Basinger human fibroblasts were used. The results are shown in Table 4, below.

TABLE 4

Cell Survival with Trehalose Combinations and Trehalose Alone

| Test Disaccharide/ Polyol | Cell Cultures | | | |
| --- | --- | --- | --- | --- |
|  | Day 3 | Day 4 | Day 5 | Day 6 |
| Trehalose with Glycerol | 49 | 37 | 18 | 9 |
| Trehalose with Mannitol | 32 | 9.6 | 4.8 | 1 |
| Trehalose | 7.5 | 0.8 | 2.2 | 1.5 |
| Control Cells | 38 | 19.5 | 9.4 | 5 |

As indicated in Table 4, the combination of trehalose with glycerol provided the greatest protective effect on cell viability, including trehalose alone. In addition, cells treated with the combination of trehalose and mannitol showed signs of toxicity and stopped growth after a few passages. In contrast, in one of the samples, cells treated with a combination of trehalose and glycerol were able to grow after 13 days of drying (about 14% of the cells were alive) and first cell passages were successful. Upon subsequent passaging, the cells do not grow well or at all.

Figure 8:
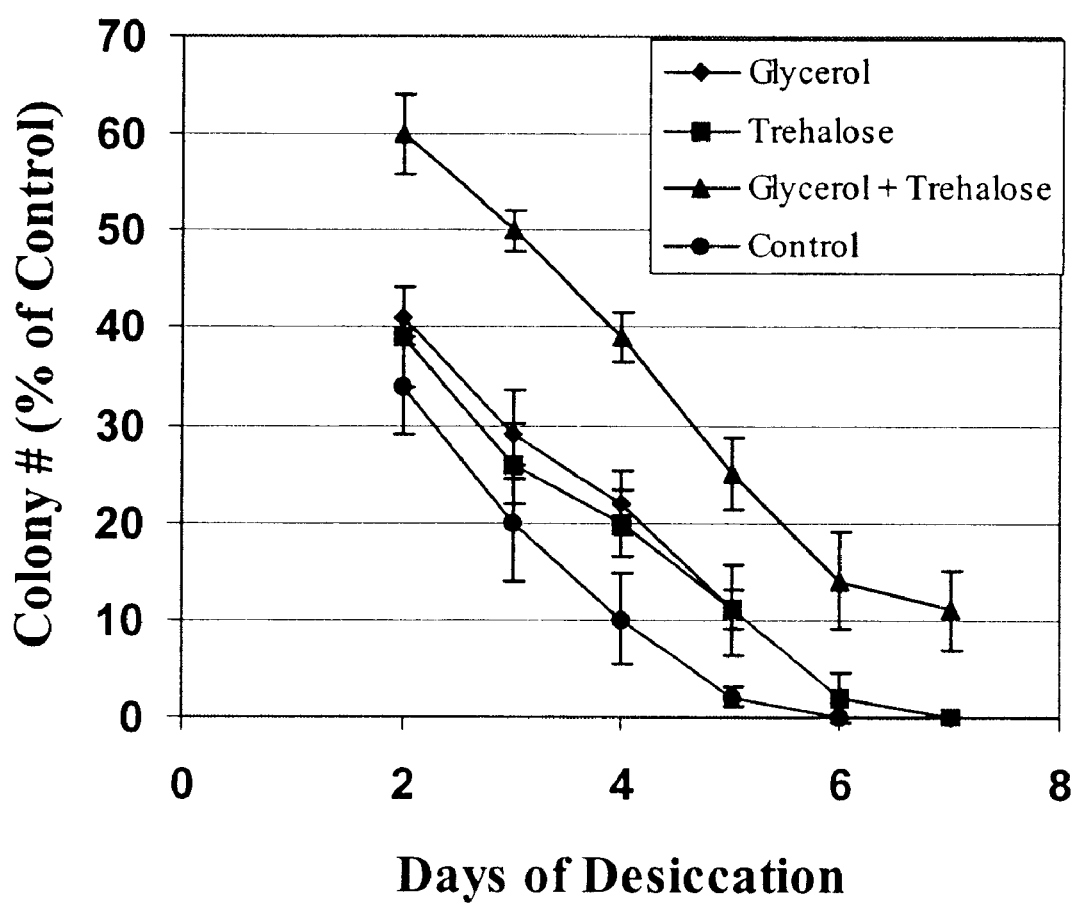
FIG. 8 provides a graft showing the effects of glycerol and trehalose alone, and in combination, on desiccation tolerance.

When used singly, glycerol and trehalose were roughly similar in their ability to mediate desiccation tolerance (See, FIG. 8). Together, an additive effect between glycerol and trehalose was observed, particularly when they were introduced by thermal shock (See, FIG. 8). Prolonged incubation with glycerol resulted in substantial toxicity and so could not be used in combination with trehalose.

In subsequent experiments, trehalose was tested in combination with glycogen, glycerol, and sucrose. As for some anhydrobiotic organisms (e.g., Artemia cysts) glycerol accounts for about 4% of their dry weight and trehalose constitutes up to about 14% of their dry weight, these experiments were conducted to determine the effects of these compounds on cell survival. The results of the trehalose and glycerol combination (as well as controls) are provided in FIG. 8. In this Figure, results are shown for Basinger cells plated in 6-well plates and exposed to 3% glycerol and/or 50 mM trehalose immediately prior to undergoing thermal shock and desiccation under vacuum. After the drying period was complete, media were added and the cells were incubated overnight. The following day, the cells were harvested and plated for viability determination using the colony assay described herein.

In preliminary experiments, it was determined that glycerol at any concentration above about 5% is toxic for 12F and Basinger cells. Even at concentrations less than 5%, cells with prolonged contact (i.e., more than about 1 hour) to glycerol, exhibited toxic effects. Thus, in these experiments, 3% glycerol was used.

EXAMPLE 9

Dried Human Cells Do Not Contain Any Detectable Water

In this Example, experiments conducted to determine whether the presence of water affected the viability of dried cells over time are described. In these experiments, the water content of dried 12F cells was measured by Fourier transform infrared spectroscopy (FTIR) after 24, 48, and 72 hours of drying.

To measure water content, the region of the water spectrum associated with stretching modes (both symmetric and asymmetric) was used. This occurs nominally at 3600–3800 $cm^{-1}$. Preliminary experiments with a number of different materials compatible with cell growth demonstrated that glass coverslips had a consistently low IR absorbance in this region, making them an ideal substrate for measuring the water content of cells grown on a two-dimensional surface.

Thus, 12F cells were grown on glass coverslips placed in 6-well plates ($3 \times 10^5$ cells/well) and infected with Ad-OTS at different MOIs. At 24, 48, and 72 hours after infection, all of the tissue culture medium was removed from the wells. The wells were then sealed with parafilm and the plates stored at room temperature for 24, 48 or 72 hours. To distinguish between IR signals arising from water and from other cellular components that might have IR absorbance in the range from 3000–3700 $cm^{-1}$, controls were also included. These controls included cultures in which confluent and subconfluent 12F cells grown on glass coverslips were baked overnight at 80° C., to remove all available water.

The FTIR spectra were recorded at room temperature in absorbance mode on a Prospect-IR FTIR spectrometer (Midac), operating with GRAMS/32 (Galactic). The mid-IR spectral region for 400 to 4000 $cm^{-1}$ was utilized. The spectra, collected by averaging 16 scans, had a resolution of 4 $cm^{-1}$, and were composed of 1868 points.

Under the conditions described above, drying occurred extremely rapidly. Three control samples that had not been dried exhibited rapid losses in water content in the approximately 5 minutes between the time that they were removed from the wells containing tissue culture medium and the time that the water content was serially measured by FTIR. Samples that had been dried had no detectable water content, compared to samples that had been baked overnight. Two baked samples were analyzed, in which the cells were grown to confluence and one in which the cells were approximately 50% confluent. The IR absorbance curves from the samples in which the cells had been dried for 24, 48, and 72 hours fell between those two curves, indicating that the water content of those samples had reached the minimum that was possible to obtain. The IR signal at 3300 $cm^{-1}$ in the baked samples could be due either to water that was so tightly bound that it was not removed from the cells even by overnight baking or to other cellular components that absorb in a similar range. Regardless, these results demonstrate that there was little or no water remaining in the dried samples, even at 24 hours, when the cells retained a high degree of viability.

EXAMPLE 10

Selection of Cells More Tolerant to Desiccation

As indicated in Example 1 above, cells that survived multiple rounds of desiccation were found to have a higher survival rate than cells that had not previously been dried. Thus, 12F cell cultures were tested for their ability to withstand multiple rounds of desiccation. All of these experiments were conducted without the addition of trehalose to the cultures. After every period of drying a vial of surviving cells was prepared and frozen. At the end of the entire experiment, the cells in all of the vials were seeded in different 6-well plates and allowed to grow to approximately 90% confluency in DMEM with 10% FBS at 37° C. The plates were then dried for five days under vacuum. At the same time, controls of nonselected cells were also grown to approximately 90–95% confluency and dried for five days as well. After five days of drying, media (DMEM) was added to the wells, and the cultures were allowed to incubate overnight at 37° C. Following this incubation, the cells were harvested and counted using a Live/Dead Viability/Cytotoxicity kit (Molecular Probes), FACS, or by trypan blue staining.

The results are shown in the following Table. In this Table, the round/days of drying are indicated, as described in Example 1. In this Table "Cont. Cells" indicates control cells.

TABLE 5

12F Cell Selection Over Drying Rounds of Various Lengths (Trypan Blue Staining)

| | Cell Cultures (number of rounds / number of days dried) | | | | | | |
|---|---|---|---|---|---|---|---|
| Cell Survival | 2r2d (S1) | 3r3d | 4r3d | 4r4d | 5r4d | 6r5d | Cont. Cells |
| % Alive | 8.8% | 14.5% | 23.4% | 29.5% | 17.5% | 6.2% | 0.9% |

Selected cells that survived after the five day drying period, typically grew well upon first passage (i.e., the first round of drying and culturing), but the growth rate tended to become slow; the cells eventually ceased growing and appeared apoptotic. Based on the results observed during these experiments, drying periods of more than 4 days resulted in a gradual decrease in the cell survival rate. Indeed, some of the selected cells that had undergone four rounds of drying were tested by passage several times and the level of viability again determined. Several attempts to transform these surviving cells were unsuccessful.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of cell biology, and/or related fields are intended to be within the scope of the following claims.

I claim:

1. A method for desiccation of mammalian cells comprising:
    a) providing at least one mammalian cell, and a means for desiccation comprising a vacuum; and
    b) exposing said at least one mammalian cell to said means for desiccation, under conditions such that said mammalian cell is desiccated and grows upon rehydration.

2. A method for desiccation of mammalian cells, comprising:
    a) providing at least one mammalian cell, and a means for desiccation comprising a vacuum; and
    b) exposing said at least one mammalian cell to said means for desiccation, under conditions such that said mammalian cell is desiccated, wherein said vacuum provides an atmosphere of less than 3% oxygen.

3. The method of claim 1, wherein said at least one mammalian cell is present in a desiccation medium comprising at least one carbohydrate.

4. A method for desiccation of mammalian cells, comprising:
    a) providing at least one mammalian cell, and a means for desiccation comprising a vacuum; and
    b) exposing said at least one mammalian cell to said means for desiccation, under conditions such that said mammalian cell is desiccated, wherein said at least one mammalian cell present in a desiccation medium is subjected to thermal shock.

5. The method of claim 3, wherein said carbohydrate is selected from the group consisting of disaccharides and polyols.

6. The method of claim 5, wherein said disaccharide is trehalose.

7. A method for desiccation of mammalian cells, comprising:
    a) providing at least one mammalian cell, and a means for desiccation comprising a vacuum; and
    b) exposing said at least one mammalian cell to said means for desiccation, under conditions such that said mammalian cell is desiccated, wherein said at least one mammalian cell is present in a desiccation medium comprising at least one carbohydrate, wherein said carbohydrate is selected from the group consisting of disaccharides and polyols, wherein said disaccharide is trehalose, and wherein said mammalian cell is capable of endogenous trehalose production.

8. The method of claim 1, wherein said mammalian cell is selected from the group consisting of adherent cells and cells in suspension.

9. The method of claim 1, wherein said mammalian cell is a human cell.

10. A method for desiccation of mammalian cells comprising:
    a) providing at least one mammalian cell, and a means for desiccation comprising a vacuum;
    b) exposing said at least one mammalian cell to said means for desiccation, under conditions such that said mammalian cell is desiccated; and
    c) maintaining said desiccated cell in a vacuum.

11. A population of desiccated mammalian cells produced according to the method of claim 1, wherein the viability of said population is greater than the viability of a second population of cells desiccated in the absence of said vacuum, and wherein said viability is determined by trypan blue exclusion after desiccation for from 2 to 5 days, rehydration, and overnight incubation in growth medium.

12. A method for desiccation of mammalian cells comprising:
    a) providing
        i) at least one mammalian cell,
        ii) desiccation medium containing at least one carbohydrate, and
        iii) means for desiccation comprising a vacuum;
    b) exposing said cell to said desiccation medium to provide a desiccation-ready cell; and
    c) exposing said desiccation-ready cell to said means for desiccation, under conditions such that said desiccation-ready cell is desiccated and grows upon rehydration.

13. The method of claim 12, wherein said vacuum provides an atmosphere of less than 3% oxygen.

14. The method of claim 12, wherein said cell is selected from the group consisting of adherent cells and cells in suspension.

15. The method of claim 12, wherein said mammalian cell is a human cell.

16. The method of claim 12, wherein said carbohydrate is selected from the group consisting of disaccharides and polyols.

17. The method of claim 16, wherein said disaccharide is trehalose.

18. A method for desiccation of cells comprising:
    a) providing
        i) at least one cell,
        ii) desiccation medium containing at least one carbohydrate, and
        iii) means for desiccation;
    b) exposing said cell to said desiccation medium to provide a desiccation-ready cell, wherein said exposing of said cell to said desiccation medium comprises thermal shock; and
    c) exposing said desiccation-ready cell to said means for desiccation, under conditions such that said desiccation-ready cell is desiccated.

19. The method of claim 12, further comprising the step of maintaining said desiccated cell under vacuum.

20. A population of cells desiccated according to the method of claim 12, wherein the viability of said population is greater than the viability of a second population of cells desiccated in the absence of said vacuum, and wherein said viability is determined by trypan blue exclusion after desiccation for from 2 to 5 days, rehydration, and overnight incubation in growth medium.

21. The population of cells of claim 20, wherein one cell in said population of cells remains viable for more than 5 days following desiccation.

22. The method of claim 1, wherein said vacuum provides an atmosphere of less than 3% oxygen.

23. The method of claim 3, wherein said at least one mammalian cell present in a desiccation medium is subjected to thermal shock.

24. The method of claim 5, wherein said mammalian cell is capable of endogenous trehalose production.

25. The method of claim 1, further comprising the step of maintaining said desiccated cell in a vacuum.

26. The method of claim 12, wherein said exposing of said cell to said desiccation medium comprises thermal shock.

* * * * *